United States Patent
Appelbaum et al.

(10) Patent No.: US 11,355,228 B2
(45) Date of Patent: Jun. 7, 2022

(54) SYSTEM, METHODS, AND APPARATUSES FOR MANAGING DATA FOR ARTIFICIAL INTELLIGENCE SOFTWARE AND MOBILE APPLICATIONS IN DIGITAL HEALTH THERAPEUTICS

(71) Applicant: BETTER THERAPEUTICS, INC., San Francisco, CA (US)

(72) Inventors: Kevin Appelbaum, Corte Madera, CA (US); Mark Berman, San Francisco, CA (US); Andres Camacho, Lafayette, CA (US); Nicole Rosendin, San Francisco, CA (US); David Merkoski, San Francisco, CA (US)

(73) Assignee: BETTER THERAPEUTICS, INC., San Francisco, CA (US)

(*) Notice: Subject to any disclaimer, the term of this patent is extended or adjusted under 35 U.S.C. 154(b) by 510 days.

(21) Appl. No.: 15/963,999

(22) Filed: Apr. 26, 2018

(65) Prior Publication Data
US 2018/0315499 A1    Nov. 1, 2018

Related U.S. Application Data

(60) Provisional application No. 62/492,065, filed on Apr. 28, 2017, provisional application No. 62/628,842, (Continued)

(51) Int. Cl.
*G16H 10/20* (2018.01)
*G16H 20/60* (2018.01)
(Continued)

(52) U.S. Cl.
CPC ............ *G16H 20/60* (2018.01); *G16H 10/20* (2018.01); *G16H 10/60* (2018.01); *G16H 15/00* (2018.01);
(Continued)

(58) Field of Classification Search
CPC ........ G16H 10/60; G16H 40/20; G16H 50/20; G16H 20/10; G16H 50/30; G16H 20/70;
(Continued)

(56) References Cited

U.S. PATENT DOCUMENTS 7,935,307 B2    5/2011    Angelides
8,066,640 B2    11/2011   Angelides
(Continued)

FOREIGN PATENT DOCUMENTS

WO    WO-2020061562 A1 *  3/2020  ........... A61B 5/0022
WO    WO 2020247032 A1    12/2020

OTHER PUBLICATIONS

Chayakrit Krittanawong, HongJu Zhang, Zhen Wang, Mehmet Aydar, Takeshi Kitai, Artificial Intelligence in Precision Cardiovascular Medicine, JACC Journals, Archives, vol. 69 No. 21, pp. 2657-2664 (Year: 2021).*

(Continued)

*Primary Examiner* — Rachelle L Reichert
*Assistant Examiner* — Teresa S Williams
(74) *Attorney, Agent, or Firm* — Todd Lorenz

(57) ABSTRACT

Disclosed herein are systems and methods of a digital therapy service to generate therapy regimen addressing a health condition, which may require the customer to perform various tasks and instruct devices to capture data related to the customer's therapy, including body metric measurements and information related to the number and quality of interactions between the user and aspects of the digital therapy service, sometimes referred to as "user-generated" inputs. The digital therapy service may calculate various metrics, such as scores and milestone determinations, to measure the customer's progress. The scores can be determined using dynamically generated and updated scoring models. Artificial intelligence chatbots may be used to (Continued)

deliver and capture information to and from customers during interactive sessions. Each customer may have a unique chatbot queue that contains the various chatbots that will be used to deliver particular aspects of the customer's therapy.

90 Claims, 5 Drawing Sheets

Related U.S. Application Data filed on Feb. 9, 2018, provisional application No. 62/629,644, filed on Feb. 12, 2018.

(51) Int. Cl.
| | |
|---|---|
| G16H 20/30 | (2018.01) |
| H04L 51/02 | (2022.01) |
| H04L 67/12 | (2022.01) |
| G16H 50/30 | (2018.01) |
| G16H 10/60 | (2018.01) |
| G16H 50/20 | (2018.01) |
| G16H 20/70 | (2018.01) |
| G16H 15/00 | (2018.01) |
| G16H 80/00 | (2018.01) |

(52) U.S. Cl.
CPC ............. *G16H 20/30* (2018.01); *G16H 20/70* (2018.01); *G16H 50/20* (2018.01); *G16H 50/30* (2018.01); *G16H 80/00* (2018.01); *H04L 51/02* (2013.01); *H04L 67/12* (2013.01)

(58) Field of Classification Search
CPC ........ G16H 10/20; G16H 20/30; G16H 15/00; H04L 67/12; H04L 51/02
USPC .......................................................... 705/2
See application file for complete search history.

(56) References Cited

U.S. PATENT DOCUMENTS

| | | | |
|---|---|---|---|
| 8,568,309 | B2 | 10/2013 | Angelides |
| 8,812,244 | B2 | 8/2014 | Angelides |
| 8,838,513 | B2 | 9/2014 | Sudharsan |
| 9,064,040 | B2 | 6/2015 | Sudharsan |
| 9,536,053 | B2 | 1/2017 | Sudharsan |
| 9,754,077 | B2 | 9/2017 | Sysko et al. |
| 9,817,559 | B2 | 11/2017 | Simon et al. |
| 9,824,190 | B2 | 11/2017 | Sudharsan |
| 9,858,394 | B2 | 1/2018 | Sudharsan |
| 9,881,136 | B2 | 1/2018 | Sysko et al. |
| 9,992,292 | B2 | 6/2018 | Gunnarsson et al. |
| 10,152,675 | B2 | 12/2018 | Sudharsan |
| 10,176,893 | B2 | 1/2019 | Sysko et al. |
| 10,192,638 | B2 | 1/2019 | Sysko et al. |
| 10,319,477 | B1 | 6/2019 | Bill |
| 10,672,509 | B2 | 6/2020 | Sudharsan |
| 10,748,658 | B2 | 8/2020 | McRaith et al. |
| 10,818,389 | B2 | 10/2020 | Sysko et al. |
| 10,839,951 | B2 | 11/2020 | Sysko et al. |
| 10,846,607 | B2 | 11/2020 | Sysko et al. |
| 10,854,337 | B2 | 12/2020 | McRaith et al. |
| 10,860,943 | B2 | 12/2020 | Sysko et al. |
| 10,872,686 | B2 | 12/2020 | Sysko et al. |
| 10,978,207 | B2 | 4/2021 | McRaith et al. |
| 2007/0072156 | A1 | 3/2007 | Kaufman et al. |
| 2007/0288266 | A1 | 12/2007 | Sysko et al. |
| 2008/0299009 | A1 | 12/2008 | Angelides |
| 2009/0264337 | A1 | 10/2009 | Angelides |
| 2010/0191075 | A1 | 7/2010 | Angelides |
| 2011/0046519 | A1 | 2/2011 | Raheman |
| 2011/0125520 | A1 | 5/2011 | Dhoble |
| 2012/0029327 | A1 | 2/2012 | Angelides |
| 2012/0231431 | A1 | 9/2012 | Angelides |
| 2013/0035563 | A1 | 2/2013 | Angelides |
| 2013/0078601 | A1 | 3/2013 | Angelides |
| 2013/0110551 | A1 | 5/2013 | Bingol |
| 2013/0117040 | A1 | 5/2013 | James et al. |
| 2013/0187780 | A1 | 7/2013 | Angelides |
| 2014/0154653 | A1 | 6/2014 | Angelides |
| 2014/0214442 | A1 | 7/2014 | Duffy et al. |
| 2014/0214443 | A1 | 7/2014 | Duffy et al. |
| 2014/0222454 | A1 | 8/2014 | Duffy et al. |
| 2014/0363794 | A1 | 12/2014 | Angelides |
| 2015/0079561 | A1 | 3/2015 | Petakov et al. |
| 2015/0281384 | A1 | 10/2015 | Gunnarsson et al. |
| 2015/0288797 | A1* | 10/2015 | Vincent ................. G16H 10/60 455/404.2 |
| 2016/0012342 | A1 | 1/2016 | Simon et al. |
| 2017/0076630 | A1 | 3/2017 | Angelides et al. |
| 2017/0109479 | A1* | 4/2017 | Vemireddy ............ G06Q 50/22 |
| 2017/0162069 | A1 | 6/2017 | Petakov et al. |
| 2017/0228520 | A1* | 8/2017 | Kidd ...................... G16H 20/13 |
| 2017/0329917 | A1 | 11/2017 | McRaith et al. |
| 2017/0329933 | A1* | 11/2017 | Brust ................ G06F 16/24575 |
| 2017/0344726 | A1 | 11/2017 | Duffy et al. |
| 2018/0180633 | A1 | 6/2018 | Volek et al. |
| 2018/0247713 | A1* | 8/2018 | Rothman ........... A61B 5/02055 |
| 2018/0277246 | A1* | 9/2018 | Zhong .................... G16H 20/10 |
| 2020/0335218 | A1 | 10/2020 | McRaith et al. |
| 2020/0383571 | A1 | 12/2020 | Fakhouri et al. |
| 2020/0383648 | A1 | 12/2020 | Bridgewater et al. |
| 2020/0388376 | A1 | 12/2020 | Kendale |
| 2020/0388381 | A1 | 12/2020 | Kozin et al. |
| 2020/0388392 | A1 | 12/2020 | Chen et al. |
| 2020/0388393 | A1 | 12/2020 | Boulos et al. |
| 2020/0388399 | A1 | 12/2020 | Kozin et al. |
| 2020/0388403 | A1 | 12/2020 | Boulos et al. |
| 2021/0035690 | A1 | 2/2021 | McRaith et al. |

OTHER PUBLICATIONS

U.S. Appl. No. 15/963,994, entitled: "Method and System for Managing Lifestyle and Health Interventions", filed Apr. 26, 2018; Published as US 2019-0074080 A1 on Mar. 7, 2019.

Barnard et al., "A low-fat vegan diet and a conventional diabetes diet in the treatment of type 2 diabetes: a randomized, controlled, 74-wk clinical trial", Am J Clin Nutr, vol. 89:1588S-1596S (2009).

Berman et al., "FareWell and the How of Lifestyle Medicine", American Journal of Lifestyle Medicine, vol. 11, No. 4, pp. 317-317 (2017).

Berman, M., "Learning & Outcomes From Our First Digital Therapeutic Pilot", (2017), pp. 1-7, URL: https://farewell-assets.s3.amazonaws.com/Pilot_Results_Extended_Referenced_Version.pdf.

Comstock, J., "FareWell raises $8.5M for digital coaching weight loss service", Mobihealthnews, Jun. 23, 2016, URL: http://www.mobihealthnews.com/content/farewell-raises-85m-digital-coaching-weight-loss-service.

Coughlin, S., "Smartphone Applications for Promoting Healthy Diet and Nutrition: A Literature Review", Jacobs J Food Nutr., vol. 2(3), pp. 1-14 (2016).

Economic Costs of Diabetes in the U.S. in 2012, Diabetes Care, vol. 36(4):1033-1046 (2013).

Jenkins et al., A dietary portfolio approach to cholesterol reduction: combined effects of plant sterols, vegetable proteins, and viscous fibers in hypercholesterolemia Metabolism 51:1596-1604 (2002).

National Diabetes Statistics Report 2017: Centers for Disease Control and Prevention, U.S. Department of Health and Human Services, URL: www.cdc.gov/diabetes/library/reports/congress/html.

Shahraz et al., "Change in testing, awareness of hemoglobin A1c result, and glycemic control in US adults, 2007-2014.", JAMA, vol. 318(18):1825-1827 (2017).

Shi, Y and Hu, FB, "The global implications of diabetes and cancer", Lancet, vol. 383(9933):1947-1948 (2014).

Gary Sforzo, "A "Digital Therapy"Using Wellcoaches Model", Wellcoaches, School of coaching, Mar. 13, 2017, Blog entry, URL: http://blogs.wellcoachesschool.com/?p=345.

(56) References Cited

OTHER PUBLICATIONS

"Worldwide trends in diabetes since 1980: a pooled analysis of 751 population-based studies with 4.4 million participants", NCD Risk Factor Collaboration (NCD-RisC): The Lancet, 387:1513-1530 (2016).

* cited by examiner

SYSTEM, METHODS, AND APPARATUSES FOR MANAGING DATA FOR ARTIFICIAL INTELLIGENCE SOFTWARE AND MOBILE APPLICATIONS IN DIGITAL HEALTH THERAPEUTICS

CROSS-REFERENCE TO RELATED APPLICATIONS

This application claims the benefit of U.S. 62/492,065, entitled "METHOD AND SYSTEM FOR MANAGING LIFESTYLE AND HEALTH INTERVENTIONS," filed Apr. 28, 2017; and U.S. 62/628,842, entitled "SYSTEMS, METHODS, AND APPARATUSES FOR MANAGING DATA FOR ARTIFICIAL INTELLIGENCE SOFTWARE AND MOBILE APPLICATIONS IN DIGITAL HEALTH THERAPEUTICS," filed Feb. 9, 2018; and U.S. 62/629,644, entitled "METHOD AND SYSTEM FOR MANAGING LIFESTYLE AND HEALTH INTERVENTIONS," filed Feb. 12, 2018, each of which are incorporated herein by reference in their entirety.

TECHNICAL FIELD OF DISCLOSURE

The subject matter disclosed herein generally relates to managing and providing digital therapeutic intervention that can provide a measurable improvement in one or more therapeutic milestone in cardiometabolic disorders such as diabetes, and can further leas to an actual reduction in pharmaceutical reliance. Some of the aspects described herein for achieving these therapeutic results include mobile applications, machine-learning, and artificial intelligence chatbots.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Despite the long-standing, massive effort to develop effective methods for increasing healthy behavior in human subjects, the number of people worldwide who suffer from adverse cardiometabolic conditions such as obesity, cardiovascular disease, and metabolic disorders (e.g., type-II diabetes) is rapidly growing. These conditions result in numerous medical complications, a lowered quality of life, shortened lifespan, lost work productivity, a strain on medical systems, and a burden on medical insurance providers, all of which translates into increased costs for both individuals and society.

Indeed, type 2 diabetes prevalence is at pandemic levels and continues to rise in the U.S. and globally. NCD Risk Factor Collaboration, *The Lancet* 387:1513-1530 (2016); Shi & Hu, *The Lancet* 383:1947-1948 (2014). Medication costs are rising in parallel and threaten to bankrupt national health systems. National Diabetes Statistics Report 2017: Centers for Disease Control and Prevention, U.S. Department of Health and Human Services (internet); Economic Costs of Diabetes in the U.S. in 2012, *Diabetes Care* 36(4):1033-1046 (2013) Despite increased use of medications and the advent of new pharmacological interventions, glycemic control among those with diabetes has not been improving since 2010. Barnard et al., Change in Testing, Awareness of Hemoglobin A1c Result, and Glycemic Control in US Adults, 2007-2014 *JAMA* 318 (8):1825-1827 (2017).

As but one example, metformin is an antihyperglycemic agent that can improve glucose tolerance in patients with type II diabetes by lowering both basal and post-prandial plasma glucose. In patients with known or suspected impaired renal function such as those with advanced age, however, metformin administration requires close dose monitoring and titration to prevent lactic acidosis, a potentially fatal metabolic complication. Patients with concomitant cardiovascular or liver disease, sepsis, and hypoxia also have an increased risk of lactic acidosis. Thus, metformin remains an unavailable and/or risky treatment for certain patient groups due to its side effects.

Similarly, the pharmaceutical and surgical interventions currently available for treatment of obesity are also associated with significant risks and costs. Until recently, obesity treatments included two FDA-approved drugs. Orlistat (Xenical®) reduces intestinal fat absorption by inhibiting pancreatic lipase, while sibutramine (Meridia®) decreases appetite by inhibiting deactivation of the neurotransmitters norepinephrine, serotonin, and dopamine, but sibutramine has now been taken off the market in the U.S. and Europe. Undesirable side-effects, including effects on blood pressure, have been reported with both these drugs. (See, e.g., "Prescription Medications for the Treatment of Obesity," NIH Publication No. 07-4191, December 2007). Moreover, surgical treatments, including gastric bypass surgery and gastric banding, are available, but only in extreme cases. These procedures can be dangerous, and furthermore may not be appropriate options for patients with more modest weight loss goals.

As yet another example, cardiac disease intervention can include statins, diuretics, ACE inhibitors, calcium channel blockers, beta blockers, alpha blockers, angioplasty, and cardiac bypass surgery. Each of these medical or surgical interventions for addressing cardiometabolic conditions are associated with significant risks and costs.

More recently, with the improvements to digital technology, efforts have been made to intervene with individuals via a digital interface, rather than simply applying conventional approaches (e.g., surgery, pharmaceuticals). These digital technologies have been developed to both collect personal biometric data from participants and to encourage their participation in established diabetes protocols, e.g., via group therapy. See, e.g., US 2013/0117040 and US 2007/0072156. Unfortunately, however, the predictive analytics employed in these platforms are generally inadequate, placing primary reliance on body metric data collection and comparative analysis against generalized body metric objectives. Moreover, subsequent interventions lack personalization and are largely historical in focus, i.e. a determination of how far the participant has progressed towards a given objective. Not surprisingly, then, compliance rates for existing digital programs directed toward behavioral changes that are targeted toward improving one or more lifestyle-related health conditions are extremely low and generally not durable over time.

As conventional treatment approaches (e.g., surgery, pharmaceuticals) are often expensive, frequently ineffective, and cannot address matters of compliance, effective digital technology solutions are still desirable. However, existing technologies are also often ineffective as discussed above. Thus, there remains a need for technological solutions for, e.g., managing therapy regimens, such as lifestyle interventions, in a manner that provides improved compliance, improved outcomes, and/or long-term durability of improved health.

Some computing services may employ artificial intelligence chatbots to communicate with end-users. As known in the art, chatbots, sometimes referred to as "expert systems," "virtual assistants," "artificial conversational entities," "instant messaging bots," "talkbots," among other names, are computer programs that implement artificial intelligence technologies, keyword recognition, and/or natural language processing, to simulate interactive communication with end-users. In many cases, a chatbot provides help or guidance for end-users accessing an online or website-based service, such as online banking or merchant websites. A chatbot may ordinarily receive different types of data (e.g., text, audio, visual) from or through an end-user's device. The chatbot may then produce textual, visual, and/or auditory outputs in response to the corresponding inputs received from the end-user's device, where the output produced by the chatbot is based on the corresponding inputs from or through the end-user's device. For instance. when a chatbot program receives text-based inputs from an end-user's computer, the artificial intelligence program modules of the chatbot (e.g., a natural language processing engine, knowledge search engine) may recognize the text and generate an appropriate response that is contextual to the end-user's input, such that the end-user is led to believe they are having a conversation with a human.

Chatbots are usually deployed in a particular purpose, such as answering questions about the inventory of a merchant website, and are thus configured with software intended to be deployed in those discrete circumstances for end-users to interact with. For instance, a chatbot will often have an artificial intelligence software engine that receives and ingests input trained to the context of its deployment, and refined according to analytics over time. Chatbots may also differ in the underlying programmed operations to be executed and the output they generate, where the operations to be executed are a result of how they perceive the context of the input. As an example, the word "fair" can refer to either mild weather or a festival. The contextual understanding and executed processes resulting from the word "fair" can differ between one chatbot of a ticket sales website and another chatbot of a weather website. Of course, it's conceivable that the ticket sale website would have to address questions about weather, or that the weather website offers outlooks for various outdoor community events. Each website in this example may have to interpret inputs and produce outputs involving mild weather expected for an upcoming festival (e.g., "Will the weather for the fair be fair?"). The natural language processing engine of each chatbot would understand the words in the context of their deployment, as dictated by their underlying knowledgebase (e.g., database and data ontology). The upshot is that chatbot programs are not infinitely deployable, because the underlying artificial intelligence engines are not tailored to understand context in the same manner; particularly across an end-user's ongoing access session and the interactive history with the website during that session. Consequently, it may be desirable for a particular website or computing service to deploy multiple chatbots for a better tailored experience for end-users. Although chatbots are often deployed on websites, they may also be used in any number of other settings as well. For example, chatbots may be a feature that is native to locally installed software, such as a video game, instant messaging, or a helpdesk or reference component of such locally installed software.

Chatbots are ordinarily deployed discretely to interact with end-users, such that when an end-user accesses a particular computing service or website, the user is typically assigned a chatbot for that particular computing service, which may include a website or web-based application, cloud-based computing service, or other computing service having remote processes performed by devices of the service provider to provide functions and features to an end-user's device. Examples of such computing services may include GOOGLE DRIVE®, MICROSOFT 365®, DROPBOX®, EVERNOTE®, and the like. As a result, there is often no continuity associating the end-user, an interactive session, various chatbots, and the underlying computing service or website. Rather, each chatbot is discretely accessed, executed, and terminated based on whichever component of the website or computing service that was accessed by the end-user to trigger the chatbot. So even though there may be more than one possible chatbot, this stovepipe approach to executing discrete chatbots can still be limiting on introducing more dynamic features, which can improve the quality of the relationship with the end-user.

Therefore, what is needed is a way for a particular computing service (e.g., native application, web-application, website) to provide and manage multiple possible chatbots that will interact with users and other devices. What is also needed is a means for preemptively identifying and providing new chatbots to provide to the user. What is also needed is a means for tracking the status and priority of chatbots, including those that may no longer be relevant to the end-user's circumstances.

SUMMARY

Disclosed herein are systems and methods intended to address the above-described shortcomings in the art but may provide additional or alternative benefits as well. A digital therapy service may create and publish a software application that provides healthcare therapeutic options as a supplement or an alternative to drugs, surgery, or other conventional treatments. Devices of the digital therapy service may be used to automatically or manually generate therapy regimen that may address a health condition of a customer of the digital therapy service, which may require the customer to perform various tasks and may instruct various devices to capture certain types of data related to the customer's therapy, including body metric measurements and information related to the number and quality of interactions between the user and aspects of the digital therapy service, sometimes referred to as "user-generated" inputs. The digital therapy service may calculate various metrics, such as scores and milestone determinations, to measure the customer's progress. The scores can be determined using dynamically generated and updated scoring models. Artificial intelligence chatbots may be used to deliver and capture information to and from customers during interactive sessions. Each customer may have a unique chatbot queue that contains the various chatbots that will be used to deliver particular aspects of the customer's therapy.

In one aspect, a computer-implemented method comprises generating, by a computer, a therapy regimen associated with a condition of a user, wherein the therapy regimen comprises one or more machine-readable computer files containing machine-executed instructions for a mobile application and indicates a set of one or more pre-stored parameters associated with the condition; receiving, by the computer, a plurality of inputs associated with the therapy regimen of the user from one or more devices via a network, wherein an input contains a value of a parameter; comparing, by the computer, the value of the parameter against a corresponding pre-stored parameter stored in a first database; determining, by the computer, a regimen status for the therapy regimen of the user based upon the value of the parameter with respect to the corresponding pre-stored parameter; and transmitting, by the computer, to a user device associated with the user a milestone achievement interface that is based on the regimen status, wherein the milestone achievement interface is configured to be displayed on a graphical user interface at the user device.

In some embodiments, when receiving the plurality of inputs the method further comprises storing, by the computer, each respective input into a user record of a second database.

In some embodiments, at least one of the inputs is a user-generated input received from the user device, and wherein the method further comprises calculating, by the computer, a score indicating a likelihood of success associated with the therapy regimen based upon a frequency of receiving each user-generated input.

In some embodiments, the method further comprises updating, by the computer, the user record of the second database to include the score indicating the likelihood of success.

In some embodiments, the computer updates the score indicating the likelihood of success at a predetermined interval.

In some embodiments, at least one of the inputs is received from a device selected from the group comprising: a coach device, a third-party server, and an artificial intelligence server.

In some embodiments, the method further comprises receiving, by the computer, via the network one or more coach inputs from a coach device; and updating, by the computer, the user record of the second database to at least one coaching input received from the coach device.

In some embodiments, the method further comprises generating, by the computer, a coaching interface configured to display the one or more coaching inputs received from the coach device; and transmitting, by the computer, the coaching interface to the user device.

In some embodiments, the method further comprises transmitting, by the computer, to the user device at least a portion of the machine-readable computer files of the therapy regimen to be executed by the mobile application of the user device.

In some embodiments, the method further comprises updating, by the computer, the therapy regimen associated with the condition of the user based upon the regimen status for the therapy regimen; and updating, by the computer, the therapy regimen and parameters in the user record of the second database.

In some embodiments, at least one input includes a body metric measurement received from a device configured to generate the body metric measurement.

In another aspect, an apparatus comprises a processor configured to: generate a therapy regimen associated with a condition of a user, wherein the therapy regimen comprises one or more machine-readable computer files containing machine-executed instructions for a mobile application and indicates a set of one or more pre-stored parameters associated with the condition; receive a plurality of inputs associated with the therapy regimen of the user from one or more devices via a network, wherein each input contains a value of a parameter; compare the value of the parameter against a corresponding pre-stored parameter stored in a first database; determine a regimen status for the therapy regimen of the user based upon the value of the parameter with respect to the corresponding pre-stored parameter; and transmit to a user device associated with the user a milestone achievement interface that is based on the regimen status, wherein the milestone achievement interface is configured to be displayed on a graphical user interface at the user device.

In some embodiments, the processor is further configured to store each respective input into a user record of a second database.

In some embodiments, at least one of the inputs is a user-generated received from the user device, and wherein the processor is further configured to calculate a score indicating a likelihood of success associated with the therapy regimen based upon a frequency of receiving each user-generated input.

In some embodiments, the processor is further configured to update the user record of the second database to include the score indicating the likelihood of success.

In some embodiments, the computer updates the score indicating the likelihood of success at a predetermined interval.

In some embodiments, at least one of the inputs is received from a device selected from the group comprising: a coach device, a third-party server, and an artificial intelligence server.

In some embodiments, the processor is further configured to receive via the network one or more coaching inputs from a coach device; and update the user record of the second database to at least one coaching input received from the coach device.

In some embodiments, the processor is further configured to generate a coaching interface configured to display the one or more coaching inputs received from the coach device; and transmit the coaching interface to the user device.

In some embodiments, the processor is further configured to transmit to the user device at least a portion of the machine-readable computer files of the therapy regimen to be executed by the mobile application of the user device.

In some embodiments, the processor is further configured to update the therapy regimen associated with the condition of the user based upon the regimen status for the therapy regimen; and update the therapy regimen and parameters in the user record of the second database.

In some embodiments, at least one input includes a body metric measurement received from a device configured to generate the body metric measurement.

In another aspect, a computer-implemented method comprises: receiving, by a computer, a therapy regimen associated with a condition of a user from a first server, wherein the therapy regimen comprises one or more machine-readable computer files containing machine-executed instructions for a mobile application and indicates a set of one or more parameters associated with the condition; receiving, by the computer, via a graphical user interface one or more inputs associated with the therapy regimen of the user, wherein an input contains a value of a parameter; comparing, by the computer, the value of the parameter against a corresponding pre-stored parameter stored in a first database; determining, by the computer, a regimen status based upon the value of the parameter with respect to the corresponding pre-stored parameter; and generating, by the computer, a milestone interface configured to display via the graphical user interface a milestone achievement based upon the regimen status.

In some embodiments, receiving the one or more inputs further comprises transmitting, by the computer, each respective input to a second database configured to store data associated with the user in a database record for the user.

In some embodiments, the method further comprise determining, by the computer, a score indicating a likelihood of success associated with the therapy regimen based upon a frequency of receiving each respective input via the graphical user interface.

In some embodiments, the method further comprises transmitting, by the computer, the score indicating the likelihood of success to the second database to update the database record for the user.

In some embodiments, the computer updates the score indicating the likelihood of success at a predetermined interval.

In some embodiments, the method further comprises receiving, by the computer, one or more body metric inputs containing one or more values, each representing a body metric measurement.

In some embodiments, at least one body metric measurement input is received from a device configured to generate the body metric measurement.

In some embodiments, the device that is configured to generate the body metric measurement is selected from the group comprising: a smart home device, a wearable device, and a fitness tracker.

In some embodiments, the method further comprises receiving, by the computer, via the network one or more coaching inputs from a coach device; and generating, by the computer, a coaching interface configured to display the one or more coaching inputs received from the coach device.

In some embodiments, the method further comprises generating, by the computer, a prompt interface at a given time according to the instructions of the therapy regimen, the prompt interface configured to display a field that receives the input from the user via the graphical user interface of the computer.

In another aspect, an apparatus comprises a processor configured to: receive a therapy regimen associated with a condition of a user from a first server, wherein the therapy regimen comprises one or more machine-readable computer files containing machine-executed instructions for a mobile application and indicates a set of one or more parameters associated with the condition; receive via a graphical user interface one or more inputs associated with the therapy regimen of the user, wherein an input contains a value of a parameter; compare the value of the parameter against a corresponding pre-stored parameter stored in a first database; determine a regimen status based upon the value of the parameter with respect to the corresponding pre-stored parameter; and generate a milestone interface configured to display via the graphical user interface a milestone achievement based upon the regimen status.

In some embodiments, the processor is further configured to transmit each respective input to a second database configured to store data associated with the user in database record for the user.

In some embodiments, the processor is further configured to determine a score indicating a likelihood of success associated with the therapy regimen based upon a frequency of receiving each respective input via the graphical user interface.

In some embodiments, the processor is further configured to transmit the score indicating the likelihood of success to the second database to update the database record for the user.

In some embodiments, the processor is configured to update the score indicating the likelihood of success at a predetermined interval.

In some embodiments, the processor is further configured to receive one or more body metric measurement inputs containing one or more values, each representing a body metric measurement.

In some embodiments, the computer receives at least one body metric input from a device configured to generate the body metric measurement.

In some embodiments, the device that is configured to generate the body metric measurement is selected from the group comprising: a smart home device, a wearable device, and a fitness tracker.

In some embodiments, the processor is further configured to receive via the network one or more coaching inputs from a coach device; and generate a coaching interface configured to display the one or more coaching inputs received from the coach device.

In some embodiments, the processor is further configured to generate a prompt interface at a given time according to the instructions of the therapy regimen, the prompt interface configured to display a field that receives the input from the user via the graphical user interface of the computer.

In another aspect, a computer-implemented method comprises: receiving, by a computer, from one or more devices associated with a user a plurality of initial inputs and an indicator of a condition of the user, wherein at least one of the devices is a mobile device, and wherein each respective initial input contains a value; storing, by the computer, each value of the plurality of initial inputs into a database that is configured to store one or more database records of the user; generating, by the computer, a health score of the user based upon: one or more values stored in a database record of the user, and the condition associated with the user; generating, by the computer, a therapy regimen based upon the health score of the user and the condition associated with the user, wherein the therapy regimen comprises one or more machine-executable instructions; and receiving, by the computer, a plurality of data inputs from the one or more devices, wherein at least one data input indicates an interaction between the user and the mobile device, and wherein each respective data input contains a value; and updating, by the computer, the health score of the user using the one or more data inputs and an amount of interactions between the user and the mobile device.

In some embodiments, generating the health score of the user further comprises generating, by the computer, a health score model associated with the condition according to a statistical analysis of one or more types of data stored in a plurality of database records of the database, and the health score model is configured to determine the health score associated with the condition of the user using: the amount of interactions between the user and the mobile device and one or more types of data corresponding respectively to a set of the one or more values for the one or more data inputs stored in the database record of the user.

In some embodiments, the method further comprises updating, by the computer, the health score model associated with the condition in response to the database storing a predetermined number of additional database records.

In some embodiments, the method further comprises updating, by the computer, the health score model associated with the condition at predetermined time interval.

In some embodiments, the method further comprises selecting, by the computer, a chatbot identifier for a corresponding chatbot for the mobile device to implement according to the therapy regimen; and updating, by the computer, a chatbot queue of the user to include the chatbot identifier.

In some embodiments, the method further comprises transmitting, by the computer, to the mobile device of the user a next chatbot identifier in the chatbot queue, wherein the chatbot queue of the user contains one or more chatbot identifiers corresponding respectively to one or more chatbots for the mobile device to implement.

In some embodiments, the health score is further based upon a frequency of receiving each of the data inputs indicating interactions between the user and the mobile device.

In some embodiments, receiving the plurality of data inputs further comprises storing, by the computer, each value of the plurality of data inputs into the one or more database records of the user.

In some embodiments, the method further comprises updating, by the computer, the therapy regimen of the user based upon the health score that is updated using the one or more data inputs and the amount of interactions.

In some embodiments, updating the therapy regimen of the user further comprises transmitting, by the computer, the therapy regimen to the mobile device of the user.

In some embodiments, a device of the one or more devices is selected from the group comprising: a smart home device, a wearable device, and a fitness tracker.

In another aspect, an apparatus comprises a processor configured to: receive from one or more devices associated with a user a plurality of initial inputs and an indicator of a condition of the user, wherein at least one of the devices is a mobile device, and wherein each respective initial input contains a value; store each value of the plurality of initial inputs into a database that is configured to store one or more database records of the user; generate a health score of the user based upon: one or more values stored in a database record of the user, and the condition associated with the user; generate a therapy regimen based upon the health score of the user and the condition associated with the user, wherein the therapy regimen comprises one or more machine-executable instructions; and receive a plurality of data inputs from the one or more devices, wherein at least one data input indicates an interaction between the user and the mobile device, and wherein each respective data input contains a value; and update the health score of the user using the one or more data inputs and an amount of interactions between the user and the mobile device.

In some embodiments, the processor is further configured to generate a health score model associated with the condition according to a statistical analysis of one or more types of data stored in a plurality of database records of the database, and the health score model is configured to determine the health score associated with the condition of the user using: the amount of interactions between the user and the mobile device and one or more types of data corresponding respectively to a set of the one or more values for the one or more data inputs stored in the database record of the user.

In some embodiments, the processor is further configured to update the health score model associated with the condition in response to the database storing a predetermined number of additional database records.

In some embodiments, the processor is further configured to update the health score model associated with the condition at predetermined time interval.

In some embodiments, the processor is further configured to: select a chatbot identifier for a corresponding chatbot for the mobile device to implement according to the therapy regimen; and update a chatbot queue of the user to include the chatbot identifier.

In some embodiments, the processor is further configured to transmit to the mobile device of the user a next chatbot identifier in the chatbot queue, wherein the chatbot queue of the user contains one or more chatbot identifiers corresponding respectively to one or more chatbots for the mobile device to implement.

In some embodiments, the health score is further based upon a frequency of receiving each of the data inputs indicating interactions between the user and the mobile device.

In some embodiments, the processor is further configured to store each value of the plurality of data inputs into the one or more database records of the user.

In some embodiments, the processor is further configured to update the therapy regimen of the user based upon the health score that is updated using the one or more data inputs and the amount of interactions.

In some embodiments, the processor is further configured to transmit the therapy regimen to the mobile device of the user.

In some embodiments, a device of the one or more devices is selected from the group comprising: a smart home device, a wearable device, and a fitness tracker.

In another aspect, a computer-implemented method comprises: receiving, by a computer, from one or more devices an input instructing the computer to update a chatbot queue associated with a user to include one or more chatbots to be implemented, wherein the chatbot queue is configured to store one or more chatbot identifiers in machine-readable storage; identifying, by the computer, a new chatbot to be implemented according to the input, and wherein each chatbot is a machine-executable program configured to be executed by an artificial intelligence server; identifying, by the computer, a chatbot identifier that uniquely identifies the new chatbot identified according to the input; updating, by the computer, the chatbot queue associated with the user to include the chatbot identifier that identifies the new chatbot; selecting, by the computer, from the one or more chatbot identifiers in the chatbot queue a first chatbot to be implemented; and transmitting, by the computer, to a mobile application on a device associated with the user the chatbot identifier of the first chatbot and variable data associated with the first chatbot.

In some embodiments, the chatbot queue of the user further contains one or more status indicators associated with each of the one or more chatbot identifiers respectively and indicating a status of each corresponding chatbot.

In some embodiments, selecting the first chatbot from the chatbot queue further comprises identifying, by the computer, the status indicator associated with each chatbot identifier.

In some embodiments, the method further comprises updating, by the computer, the status indicator corresponding to the first chatbot according to a status update received from the mobile application at the user device.

In some embodiments, the computer selects the first chatbot upon the computer determining that the status of the first chatbot is available to be implemented.

In some embodiments, the method further comprises receiving, by the computer, a second input from at least one device of the one or more devices instructing the computer to update the status indicator corresponding to a second chatbot to at least one of invalid, unavailable, and expired.

In some embodiments, the method further comprises removing, by the computer, from the chatbot queue the chatbot identifier for the second chatbot in response to determining that the status indicator corresponding to the second chatbot indicates that the status of the second chatbot is at least one of invalid, unavailable, and expired.

In some embodiments, the status is selected from the group comprising: ready, dispatched, started, completed, invalid, expired, and deleted.

In some embodiments, the variable data comprises data stored in one or more data fields of one or more databases; and the method further comprises updating, by the computer, the data stored in a data field of a database identified by the variable data according to updated data received from at least one of the mobile device and the artificial intelligence server.

In some embodiments, selecting the chatbot identifier of the first chatbot to be implemented further comprises establishing, by the computer, a session with the mobile application of the user device.

In some embodiments, the computer and the artificial intelligence server are a same physical computing device.

In another aspect, an apparatus comprises: a processor configured to: receive from one or more devices an input instructing the processor to update a chatbot queue associated with a user to include one or more chatbots to be implemented, wherein the chatbot queue is configured to store one or more chatbot identifiers in machine-readable storage; identify a new chatbot to be implemented according to the input, and wherein each chatbot is a machine-executable program configured to be executed by an artificial intelligence server; identify a chatbot identifier that uniquely identifies the new chatbot identified according to the input; update the chatbot queue associated with the user to include the chatbot identifier that identifies the new chatbot; select from the one or more chatbot identifiers in the chatbot queue a first chatbot to be implemented; and transmit to a mobile application on a device associated with the user the chatbot identifier of the first chatbot and variable data associated with the first chatbot.

In some embodiments, the chatbot queue of the user further contains one or more status indicators associated with each of the one or more chatbot identifiers respectively and indicating a status of each corresponding chatbot.

In some embodiments, to select the first chatbot from the chatbot queue the processor is further configured to identify the status indicator associated with each chatbot identifier.

In some embodiments, the processor is further configured to update the status indicator corresponding to the first chatbot according to a status update received from the mobile application at the user device.

In some embodiments, the processor selects the first chatbot upon determining that the status of the first chatbot is available to be implemented.

In some embodiments, the processor is further configured to receive a second input from at least one device of the one or more devices instructing the processor to update the status indicator corresponding to a second chatbot to at least one of invalid, unavailable, and expired.

In some embodiments, the processor is further configured to remove from the chatbot queue the chatbot identifier for the second chatbot in response to determining that the status indicator corresponding to the second chatbot indicates that the status of the second chatbot is at least one of invalid, unavailable, and expired.

In some embodiments, the status is selected from the group comprising: ready, dispatched, started, completed, invalid, expired, and deleted.

In some embodiments, the variable data comprises data stored in one or more data fields of one or more databases; and the processor is further configured to update the data stored in a data field of a database identified by the variable data according to updated data received from at least one of the mobile device and the artificial intelligence server.

In some embodiments, to select the chatbot identifier of the first chatbot to be implemented by the user device, the processor is further configured to establish a session with the mobile application of the user device.

BRIEF DESCRIPTION OF THE DRAWINGS

The accompanying drawings, which are incorporated herein and form a part of the specification, illustrate embodiments of the present disclosure and, together with the description, further serve to explain the principles of the disclosure and to enable a person skilled in the relevant art to make and use the disclosure.

DETAILED DESCRIPTION

Figure 1:
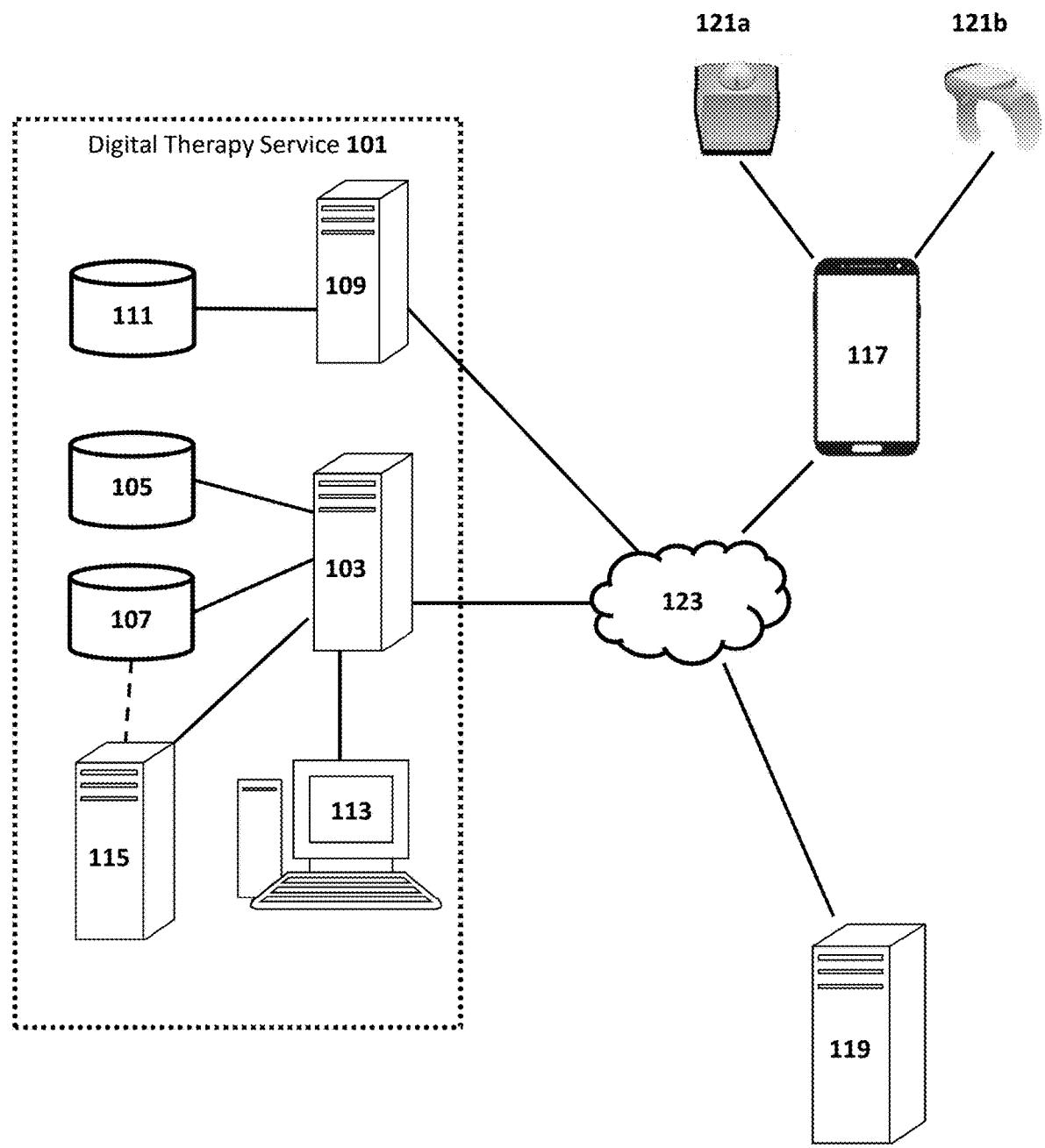
FIG. 1 shows components of a system, according to an exemplary embodiment.

Certain illustrative aspects of the systems, apparatuses and methods according to the present invention are described herein in connection with the following description and the accompanying figures. These aspects are indicative, however, of but a few of the various ways in which the principles of the invention may be employed and the present invention is intended to include all such aspects and their equivalents. Other advantages and novel features of the invention may become apparent from the following detailed description when considered in conjunction with the figures.

In the following detailed description, numerous specific details are set forth in order to provide a thorough understanding of the invention. In other instances, well known structures, interfaces and processes have not been shown in detail in order not to unnecessarily obscure the invention. However, it will be apparent to one of ordinary skill in the art that those specific details disclosed herein need not be used to practice the invention and do not represent a limitation on the scope of the invention, except as recited in the claims. It is intended that no part of this specification be construed to effect a disavowal of any part of the full scope of the invention. Although certain embodiments of the present disclosure are described, these embodiments likewise are not intended to limit the full scope of the invention.

A digital therapy provider may host a digital therapy service and may create and publish a therapeutic software application that provides healthcare therapeutic options as a supplement or an alternative to drugs, surgery, or other conventional medical treatments. Customers of the digital therapy provider may install the therapeutic software application onto a customer device (e.g., mobile device, laptop computer, workstation computer, server), and then the customer may use the customer device to load, execute, and access the various features of the software application. When initially registering with the digital therapy service or otherwise beginning to use the application, a customer may indicate a particular health condition (e.g., diabetes, high blood-pressure, high cholesterol) to be addressed and may then provide certain initial data inputs, which the digital therapy service may use to prepare an appropriate therapy regimen to address the indicated condition. The customer may then access the features of the software application to begin tasks assigned to them by the therapy regimen, such as a diet or exercise routine, among other possible tasks. The software application may provide customers with various graphical user interfaces (GUIs) that allow the customer to, for example, interact with the features of the software application in a human-friendly way, submit data inputs, log journal entries of the customer's progress, and receive information and/or feedback related to their treatment and therapy regimen.

Unlike conventional consumer-facing health, diet, fitness, and lifestyle software applications, sometimes called "apps" when installed and executed on a mobile device, the features of the software application of the digital therapy service described herein are a medical prescription, as opposed to general "well-being" tracking. Conventional well-being software products are essentially "voluntary" products that are premised on a user's voluntary participation and cue off the user's selected goals, so the functionality is broadly open to user changes and at-will interactions, but not premised on adherence to a particular regimen or other set of tasks. As the digital therapy service software described herein is subject to a medical prescription, a customer's therapy regimen is determined for a customer of the digital therapy provider, algorithmically and/or according to inputs from personnel of the digital therapy provider, with little or no input from the customer. Likewise, because activities (e.g., meals, exercise, journal entry) assigned to the customer according to the therapy regimen are "dosages" that are part of a medical prescription, rather than a generic well-being improvement effort, the customer must adhere to the therapy regimen. The software described herein may comprise various features and functions that facilitate customer adherence and track customer adherence to a therapy regimen, in a way that conventional software applications do not.

Embodiments of the systems and methods disclosed herein may include one or more computing devices, such as an operations server or any other computing device, that may calculate a health score for each customer. In many instances, a health score may be a representation of a customer's progress, the status of the customer's therapy regimen, and/or a likelihood of success. A computing device may execute one or more artificial intelligence and/or machine learning software programs to generate and update health score modeling algorithms, and/or generate and update the health scores of customers. One having skill in the art would recognize that the artificial intelligence and machine learning software may execute various artificial intelligence and machine learning algorithms and processes, such as generalized linear models, random forests, support vector machines, unsupervised and/or supervised clustering, and deep learning (e.g., neural networks), among others. In some examples, machine learning software may "learn" (e.g., update data processing algorithms according to historical data trends) from training data, which, in some instances, includes labeled data. An operations server may apply a health score model to calculate a health score, where the health score model may indicate parameters (e.g., data fields) and/or relative-weights for the parameters when calculating a corresponding health score. The health score and the corresponding health score model may be a function, at least in part, of the interactions between the customer and aspects of the digital therapy service (e.g., software application, chatbots, coach). As described herein, the health score is based on a health condition that the customer wishes to address using the features and functions provided by computing devices of the digital therapy service and the customer's device. As described herein, the health score is calculated by an operations server or other computing device of the digital therapy service using health score models that accept parameters that are relevant to the customer's health condition, where the parameters correspond to expected types of data stored in certain data fields. For instance, the health score of a customer addressing diabetes may be calculated by the operations server using a health score model that is trained with and uses data fields relevant to monitoring diabetes, such as blood glucose level and weight.

However, it should be appreciated that health scores may be tailored to calculate values representing broader or narrower qualities of a customer. As an example, a health score may represent an "overall" health status of a customer. In this example, the corresponding health score model may be trained with and use a plurality of data fields, such that the operations server or other computing device applying a health score model outputs a calculated value representing a broad understanding of the customer's health. As another example, the health score may more narrowly represent the customer's progress in addressing diabetes with respect to middle-aged males. In this example, the health score is more narrowly tailored to the customer. Because the health scores and the corresponding health score models may vary, it could also be appreciated that the operations server or other computing devices of the digital therapy service may calculate any number of health scores for customers of the digital therapy provider. For instance, a customer may receive a health score that is relative to their progress and/or therapy regimen status in addressing a health condition, and a health score that represents their overall health. The health score, in many implementations, may be determined by an operations server or other computing device using baseline body metric measurements and a series of updated data values received from, for example, a customer device at certain times over the course of treatment. In this way, the health score may be based, in part, on the customer's personal progress and/or the status of their therapy regimen.

A health score model applied by an operations server or other computing device of the digital therapy service may be trained and re-trained using any number of known statistical and regression algorithms against a predetermined set of data fields (e.g., blood glucose, cholesterol, blood pressure, weight, number of interactions with the software or coach). Any number of supervised learning techniques can be used to train a health score model. For example, in some cases a random forest regression can be trained on historical data for diabetes patients to predict A1C loss, where the historical data may be, for example, database records for individuals who have a diabetes health condition as indicated by one or more data fields of the database records. In this diabetes-related exemplary health score model, a target variable, A1C values or loss, is continuous. In another example, a gradient boosted classifier can be trained on historical database records for individuals, to determine a likelihood for whether or not a customer is going to lose over 5% of a body weight value in 12 weeks. In this exemplary model, the target variable may be a binary value (e.g., 1 or 0).

The operations server, or other device of the digital therapy service, may retrain health score models at given time intervals or when certain events occur. For instance, the operations server may retrain a health score model for a condition each time a threshold number of customers complete a therapy regimen addressing the condition. In some cases, health score models may be tailored to be applied only at a certain moment in a customer's therapy timeline. For example, a customer may receive a 12-week therapy regimen to address high blood-pressure, where the customer's health score is calculated and updated each week. In this example, the health score after the third week is calculated using a health score model that was trained using the data records of other customers treated for high blood-pressure after three weeks. A different health score model is then applied after each successive week. In such cases that use timeline-based health score models, the operations server may retrain a health score model after being used for calculations a threshold number of times.

The operations server may retrain the health score models either with or without input from personnel of the digital therapy service. In an automated implementation, the operations server may retrieve values of certain data fields from customer records that are stored in a customer database, and may then reapply the particular training algorithm. In some cases, the values of the data fields may include health scores calculated for the customers of the customer records and/or the number of interactions between such customers and the software or a coach. In implementations involving personnel of the digital therapy provider, an administrator or other person, may review the data records and manually retrain the health score model via a graphical user interface (GUI) by, for example, manually adjusting algorithms used to train a health score model and/or adjust the algorithm that is actually used by the health score model to calculate a health score.

In addition or as an alternative to sophisticated health score calculations and handling health score models, an operations server or other computing device of the digital therapy service may compare one or more data fields relevant to the customer's condition, against pre-stored milestone parameters or data values. For example, a database record for a customer addressing diabetes may have data fields for blood glucose levels and weight, among others. At certain predetermined milestone intervals, the operations server may compare the customer's recent blood glucose level against a pre-stored blood glucose level. The pre-stored milestone values may operate as threshold values that may trigger certain functions in the operations server or other devices, such as generating a notification interface to be presented at the GUI of a coach computer when a customer's data value fails to satisfy the corresponding pre-stored milestone value. In some implementations, there may be multiple pre-stored milestone values for multiple data fields, which may cause the operations server to compare multiple different customer values of different fields against multiple different pre-stored values. Additionally or alternatively, in some implementations, there may be multiple pre-stored values for a data field, such that the pre-stored values function as, for example, upper-bound and lower-bound thresholds, thereby facilitating more potential responses from the operations server.

A health score value may be applied by the digital therapy service in a number of ways. The health score value may be used to determine whether the customer is compliant with their assigned treatment. Customers may be required to conduct regular meetings with a coach to discuss their treatment. The health score value may be useful to prepare for and conduct the meeting. It is also useful for determining how the treatment is progressing generally. As such, the operations server may retrieve the health score value from the customer's data records and transmit it to a customer device or coach computer, where the health score may be presented to the customer or the coach on one or more GUI displays. In addition, a GUI may display a customer's health score value with other health score values, such as an average health score value or other customers' health score values. In this way, the customer or coach may understand the customer's health score with wider context.

A health score or milestone determination may be used to vary a customer's therapy regimen. For example, a customer whose weight fails an upper bound threshold may receive updated diet instructions. In operation, after the operations server determines the weight value of the customer's data record fails a pre-stored value for weight, one or more data fields pertaining to the customer's diet instructions may be updated to include foods having less fat or sugar. The operations server may also update the customer's chatbot queue to include a chatbot configured to display suggestions for improving the customer health score or satisfying a milestone comparison. In some cases, determining whether the data values satisfy one or more pre-stored values may be indicator of the customer's progress through their therapy regimen and/or an indicator of the status of the therapy regimen.

As a component of determining a customer's milestones, calculating scores, and/or monitoring their progress generally, the operations server may receive indicators of interactions between the customer and aspects of the digital therapy service (e.g., coach, therapeutic software application). The indicators of interactions may be received by operations server as data received from various devices (e.g., customer device, coach device, data contribution device). The operations server may use these indicators to track an amount of interactions between the user and various aspects of the digital therapy service. In some circumstances, the therapy regimen of a customer requires the customer to have a certain amount of interactions with a coach and the therapeutic software application, and the indicators of interactions may allow the operations server or a coach to review the customer's engagement and involvement with their therapy regimen. Non-limiting examples of indicators of interactions may include whether a meal plan was followed; whether a therapy regimen task was completed; whether a coaching call was completed; whether one or more, or all, ingredients on a shopping list were procured; whether the subject consumed a specified amount of water or whether the subject consumed water; a number of meal plan meals consumed, a number of tasks completed, a total number of calories burned in one or more activities, a number of coaching calls completed, length of one or more coaching calls, a number or fraction of ingredients procured from a shopping list, a number of hydration events, or a total volume of hydration.

Embodiments of the systems and methods disclosed herein may dynamically manage a queue of artificial intelligence chatbots to be provided to the customer device. Chatbots may be artificial intelligence software code of the digital therapy service's software application, where the software code may include, for example, machine-readable and/or machine-executable program modules, code, scripts, computer files, data, and the like. The chatbots allow the digital therapy service to interact with customers in a way that delivers information or instructions to customers, and dynamically responds to customer inputs or questions. Using chatbots to deliver information and field questions may beneficially provide customers with a more familiar and comfortable experience, thus increasing the likelihood of customer interactions. Chatbots may also quickly capture information that may be applied in other aspects of the digital therapy service, and reduce the demands on personnel of the service provider (e.g., coaches, administrators).

Computing devices, such as artificial intelligence servers, may have artificial intelligence software that enables such devices to execute chatbot code. Conventional approaches to providing end-users with chatbots are often static, such that end-users are provided with a particular chatbot for given session and to provide a service to an end-user that is relevant to certain circumstances. But embodiments disclosed herein may have chatbot queues that are unique to each customer of the digital therapy service, allowing the digital therapy service to provide customers with any number of chatbots configured and trained to address a particular requirement or offer a particular service. As it is a typical to provide customers multiple artificial intelligence chatbots as a means of interfacing with many components and features of a computing service like the digital therapy service, a person skilled in the art could find it unusual to employ a queue unique to each end-user for managing the dynamically changing list of artificial intelligence chatbots to be provided to an end-user.

Components of an Exemplary System Architecture

FIG. 1 shows components of a system 100, according to an exemplary embodiment. The exemplary system 100 may comprise a digital therapy service 101 of a digital therapy provider, customer devices 117 (sometimes referred to as "mobile devices" or "user devices" herein), data contribution devices 121, third-party servers 119 of third-party digital service providers, and one or more networks 123 that communicate data between the various components. In an embodiment of the exemplary system 100, the digital therapy service 101 may comprise operations servers 103, customer databases 105, application databases 107, artificial intelligence servers 109, chatbot databases 111, application servers 115, and coach computers 113 and other devices of service personnel. It should be appreciated, however, that a digital therapy service 101 may comprise any number of computing devices (e.g., servers, workstations, laptops) and networking devices (e.g., routers, switches, firewalls) configured to perform various processes and tasks described herein.

For ease of explanation, only one of each device is shown in FIG. 1. However, one having skill in the art would appreciate that some embodiments may comprise any number of devices, which may function in a distributed-computing environment for redundancy and/or load-bearing purposes. It should also be appreciated that such devices may be embodied on the same device or split among many devices, such that a single computing device may perform the functions described herein as being performed by multiple devices, or such that multiple computing devices may perform the functions described herein as being performed by a single device. For example, in some embodiments, certain processes and features described herein as being executed and provided by an operations server 103 may be distributed among and executed by a number of computing devices, which consequently execute such processes and provide such features of the operations server 103. As another example, in some embodiments, an operations server 103 may be configured to execute one or more processes and provide the features described herein as being executed and provided by an artificial intelligence server 109.

As mentioned, the devices of the system 100 may communicate via one or more networks 123. A network 123 may comprise one or more devices that communicate data between devices of the system 100. The components of a network 123 may operate using any number of communications protocols and devices for communicating data among devices, which may include one or more combination of public and/or private networks. In some circumstances, protocols may include telecommunications technology allowing for data and voice data exchange, such as 4G, 3G, LTE, and the like. In such circumstances, the network 123 may comprise telecommunications towers, routers, switches, and trunks. In some circumstances, protocols may include other types of connection-oriented or connectionless data communications protocols, such as Ethernet, TCP/IP, UDP, multiprotocol label switch (MPLS), and the like. As an example, in FIG. 1, a customer device 117 may be a mobile device that communicates with an operations server 103 and a third-party server 119 over one or more networks 123. As such, the customer device 117 may communicate (e.g., transmit and receive) data packets with a telecommunications system of a wireless mobile carrier. Towers, routers, switches, and trunks of the telecommunications system may route the data packets with an internet service provider (ISP) of the digital therapy service 101. Routers, switches, and other devices of the ISP may route the data packets to the operations server 103, or other gateway device (e.g., router, firewall), of the digital therapy service 101. In this example, the network 123 may comprise the various devices and components used to communicate the data packets between the digital therapy service 101 and the customer device 117. One having ordinary skill in the art would appreciate that the devices of the system 100 may communicate over any number of communication devices and technologies, capable of facilitating networked communication between computing devices, such as, LAN, WAN, InfiniBand, 3G, 4G, or any other computing communication means.

In addition, one having skill in the art would appreciate that devices of the digital therapy service 101 may communicate data via one or more internal computing networks using any number of networking devices (e.g., routers, switches, trunks, towers) and protocols (e.g., Bluetooth®, TCP/IP, 4G, LTE) capable of transmitting data between devices. In some implementations, internal networks of the digital therapy service 101 may be private network that are logically and/or physically separated from the network 123 components used by devices that are logically external to the digital therapy service 101, such as customer devices 117 and third-party servers 119. For example, an operations server 103 and an artificial intelligence server 109 may be physically located in different geographical locations, but may communicate over public data communications infrastructures of one or more networks 123 (e.g., Internet) using data security measures (e.g., virtual private network (VPN) protocols) to logically separate the internal computing network of the digital therapy service 101 from a more public data communications infrastructure.

An operations server 103 of the digital therapy service 101 may generate, manage, and update data associated with customers and customer therapy regimens. The operations server 103 may be any computing device comprising a processor and machine-readable memory capable of performing various processes described herein. Non-limiting examples of an operations server 103 may include a workstation computer, a laptop, server, mobile device (e.g., smartphone, tablet), and the like. As described herein, the operations server 103 may perform any number of processes driving the technical features of the digital therapy service 101, and generally providing customers therapeutic services. However, it should be appreciated that the features of the operations server 103 may be performed by, or otherwise distributed among, any number of computing devices.

In operation, the operations server 103 may execute various processes that allow the operations server 103 to function as an entryway to the features of the digital therapy service 101. The operations server 103 may receive inputs from customer devices 117 and transmit to the customer devices 117 various data files and executable instructions, where the customer devices 117 may, in some cases, execute therapeutic software published by the digital therapy provider that owns, builds, and/or operates the digital therapy service 101. The operations server 103 may be accessed by customers through the therapeutic software, which allows customers to interact with the various services and features offered by the digital therapy service 101. The operations server 103 may generate, manage, and update customer health and treatment related data, based on data inputs received from, for example, coach computers 113 or other administrator devices, customer devices 117, and third-party servers 119, among other possible devices.

In some implementations, an operations server 103 may generate a therapy regimen to treat a particular condition indicated by a customer through a graphical user interface (GUI) of a customer device 117, or indicated by a coach through a GUI of a service provider device. The operations server 103 may receive data inputs associated with treating the customer's condition or therapy regimen, sometimes referred to herein as "parameters," from various data sources, such as the customer device 117. The operations server 103 may use the incoming data to calculate various scores, such as a health score, to indicate a customer's likelihood of success and/or progress toward improving their health with respect to the condition or overall health.

The operations server 103 may comprise a comparison engine, which may be software code that may output a prediction of likelihood of a milestone achievement based on the pre-stored data from prior customers' data records. The operations server 103 may determine the likelihood of success as a function of engagement with the digital interface (e.g., number of interactions between a customer and the therapeutic software application), engagement with the lifestyle regimen (e.g., rate of compliance with therapy regimen activities, meal plans, and the like). The likelihood may also be determined as a function of one or more parameters. For example, the likelihood can be determined as a function of whether a meal plan was followed or logged; or if not, whether a meal fallback was consumed or logged; whether a lifestyle regimen activity was completed or logged; whether a coaching call was completed or logged; whether ingredients on a lifestyle regimen shopping list were procured or logged; whether the customer consumed a specified amount of water or whether water-intake was logged; a number of meal plan meals consumed, a number of activities completed, a total number of calories burned in one or more activities, a number of coaching calls completed, length of one or more coaching calls, a number or fraction of ingredients procured from a shopping list, a number of hydration events, a total volume of hydration logged, or a number or rate of body weight measurements performed. In some cases, the likelihood can be determined as a function of type or amount of, for example, physical activity completed and/or logged.

In some cases, the likelihood is determined by a multifactorial weighted analysis of two or more, three or more, four or more, five or more, six or more, seven or more, eight or more, or all types, amounts, or rates that inputs for certain customer-performed tasks are received (e.g., engagement with interface, engagement with therapy regimen, parameters, and/or type of, for example, physical activity completed). The weights and task types can be identified manually via a GUI or computationally via, for example, logistic regression or machine learning, methods to identify patterns associated with a high or low likelihood of therapeutic milestone achievement. For example, if a customer enters a low number of customer-related inputs compared to a predetermined relative threshold (e.g., relative to other members of a customer cohort, or relative to prior customers in the database, or a portion thereof) into a GUI of the customer device 117, the comparison engine of the operations server 103 may determine that the customer is unlikely to achieve a lifestyle-related health condition milestone. As another example, if a customer enters a high number of customer-related inputs into a GUI of the customer device 117 compared to a predetermined relative threshold, the comparison engine of the operations server 103 may determine that the customer is likely to achieve a lifestyle-related health condition milestone.

As another example, if a customer enters into a GUI of the customer device 117 a number of meal plan meals the customer consumed that satisfies a predetermined threshold, the comparison engine of the operations server 103 may determine that the subject is likely to achieve a lifestyle-related health condition milestone. As yet another example, if a customer enters into a GUI of the customer device 117 a low number of meal plan meals consumed compared to a predetermined threshold, the comparison engine of the operations server 103 may determine that the customer is unlikely to achieve a lifestyle-related health condition milestone.

In some implementations, based on certain data inputs or calculations generated by the operations server 103, the operations server 103 may automatically execute certain processes (e.g., load a chatbot into a chatbot queue) or instruct other devices (e.g., the customer device 117) to execute processes.

The therapy regimen may be a collection of machine-readable data and executable code that inform operation of a therapeutic software application that is published by the digital therapy service 101 and is executed by the customer device 117. For instance, the software code of the therapeutic application may be configured to generate one or more interactive GUIs according to instructions of the therapy regimen. The operations server 103 may generate tasks for customers and coaches to perform, such as diet routines, exercise routines, and coaching sessions. Details regarding the tasks may be presented to customers and coaches via the interactive GUIs, and the customers and coaches may input data as well. The operations server 103 may also execute any number of automated processes according to certain executable code as part of the therapy regimen. For example, code associated with a therapy regimen addressing a diabetes condition may, at a predetermined time, instruct the operations server 103 to query blood glucose data of a customer in a customer database 105 and then compare that blood glucose data against pre-stored blood glucose data in an application database 107. As another example, code associated with the therapy regimen may instruct the operations server 103 to add a number of chatbot identifiers to a customer's chatbot queue, which the operations server 103 may transmit to the customer device 117 for implementation.

The operations server 103 may perform a number of additional features and processes, as explained further herein. These additional processes may include, but are not limited to: tracking a customer's progress through their therapy, generating health score models and calculating health scores; identifying milestone achievements; and managing access to various features of the digital therapy service 101 through user login procedures. It should be appreciated that this listing is merely exemplary and is not intended to be exhaustive.

In some embodiments, customers and other users (e.g., coaches) may access the operations server 103 through a web-based interface. In such embodiments, the operations server 103, or other computing device of the digital therapy service 101, may execute a webserver application (e.g., Apache®, Microsoft IIS®), which may provide remote devices to access the features and processes of the operations server 103 and, more generally, the digital therapy service 101 using typical web-technology protocols (e.g., TCP/IP, HTTP). In some implementations, software applications executed by the devices of the system 100, such as a customer device 117 or a service provider device (e.g., coach computer 113), may provide native interfaces, such that a user does not require a web browser to remotely access the digital therapy service 101.

As mentioned, the system 100 may comprise one or more databases storing data related to customer services and application execution. Computing devices of the system 100, such as an operations server 103 and artificial intelligence server 109, may query and update the various databases. It should be appreciated that a database may be hosted on any computing device comprising non-transitory machine-readable storage and a processor capable of querying, retrieving, and updating data records of the database. In some embodiments, a database may be a single device hosting the database. And, in some embodiments, the contents of a database may be distributed among a plurality of computing devices. The databases in the exemplary system 100 of FIG. 1 may include an application database 107, a customer database 105, and a chatbot database 111, though one having skill in the art would appreciate that other embodiments may include additional or alternative databases, or may consolidate such databases.

An application database 107 may store data records containing data used for application operation, where the fields of such data records contain various types of data related to the processes executed by, for example, the operations server 103 and the customer device 117, among other possible devices of the system 100. An application database 107 may be hosted on any number of computing devices comprising non-transitory machine-readable storage and a processor capable of querying, retrieving, updating, and otherwise managing the data of the application database 107.

In some implementations, an application database 107 may contain data records used for selecting, generating, and/or providing therapy regimens for customer devices 117 to access via an application of the customer device 117. As mentioned, the application database 107 may contain identifiers for certain executable code to be executed by the operations server 103 or customer device 117 at certain times or in response to certain events. For example, executable code associated with the therapy regimen may instruct the operations server 103 to add a chatbot identifier to a customer's chatbot queue.

In some implementations, an application database 107 may contain data records used for generating and updating scores and/or milestone data for customers. The application database 107 may store health score models that the operations server 103 may access to calculate a customer's health score or when the operations server 103 is instructed to retrain the health score model. Similarly, the application database 107 may contain pre-stored milestone data that the operations server 103 may access to determine whether the customer has achieved a particular milestone in their treatment, based a comparison of customer data and the pre-stored milestone data by the operations server 103.

In some embodiments, the digital therapy service 101 may comprise an application server 115. In such embodiments, an application database 107 may store data associated with one or more software applications executed by the application server 115. An application server 115 may provide any number of computing services (e.g., calendar, email) to devices and/or users of the digital therapy service 101. The application server 115 may access the application database 107 as necessary to perform various features. Moreover, in some cases other devices of the digital therapy service 101 (e.g., artificial intelligence server 109, coach computer 113) may directly or indirectly (e.g., via the operations server 103) query or otherwise access the application database 107. For example, a scheduling chatbot being executed by the artificial intelligence server 109 may prompt the customer to schedule a call with a coach. The artificial intelligence server 109 may directly or indirectly query the application database 107 to determine the coach's availability for a call, and then transmit the results to the customer device 117 via an ongoing chat interface.

Like other devices described herein, an application server 115 may be any computing device comprising a processor and a machine-readable storage medium capable of performing the various tasks and processes described herein. Non-limiting examples of an application server 115 may include a workstation computer, laptop computer, a server, mobile device (e.g., smartphone, tablet), and the like.

In some embodiments, third-party servers 119 of third-party service providers may host or may otherwise be associated with various software applications (e.g., GOOGLE®, FITBIT®). A third-party server 119 may provide any number of computing services or web-based applications, such as a web-based calendar service (e.g., GOOGLE CALENDAR®, MICROSOFT 360®) or services associated with data contribution devices 121 (e.g., smart home devices, wearable devices). The data generated or otherwise hosted on such third-party servers 119 may be updated, queried, and otherwise accessed by various devices of the system, such as a customer device 117 or operations server 103. For example, a customer device 117 may receive body measurement data from a wearable fitness tracker device 121b, and then forward that data to a third-party server 119 for storage. Using application programming interfaces (APIs) of the third-party service, the customer device 117 or operations server 103 may access that data to update the customer's data record in the customer database 105. As another example, a scheduling chatbot being executed by the artificial intelligence server 109 may prompt the customer to schedule a call with a coach. The artificial intelligence server 109 may directly or indirectly query an application database 107 to determine the coach's availability for a call, and the artificial intelligence server 109 or operations server 103 may access a third-party server 119 hosting a calendar service (e.g., GOOGLE CALENDAR®) to determine the customer's availability. The operations server 103 or artificial intelligence server 109 may then reconcile the retrieved schedules to identify free time in the two calendars. The chatbot of the artificial intelligence server 109 may then output suggested times for the next meeting to the customer device 117 via an ongoing chat interface.

A customer database 105 may store customer profile data records that contain data fields for various types of data describing customers or related to customer therapy. Non-limiting examples of information stored in customer profile records may include basic information about the customer (e.g., name, date of birth, occupation), a customer identifier (customer ID), health-related data (e.g., body metric measurement data, a condition, therapeutic goal), treatment related-data (e.g., calculated scores, text of journal entries, text of coach interactions, customer-application interactions), and the like. In operation, thus customer database 105 may respond to query and update requests that are received from an operations server 103 or other devices of the system 100.

A chatbot database 111 may store machine-executable code for particular chatbots that may be executed by an artificial intelligence server 109. As mentioned, the chatbot database 111 may be hosted on any number of computing devices comprising a processor and/or machine-readable medium capable of storing, querying, updating, and otherwise managing data records associated with chatbots. A data record of the chatbot database 111 may comprise one or more data fields with data describing a chatbot or otherwise used by the chatbot. Each data record may contain a chatbot identifier field for the particular chatbot code, which the artificial intelligence server 109 may reference to access and execute the corresponding chatbot, which may be done in response to a request received from a customer device 117.

An artificial intelligence server 109 may execute machine-readable chatbot code that is stored in a chatbot database 111. The artificial intelligence server 109 may be any computing device comprising a processor and machine-readable memory capable of performing the various processes and tasks described herein. Non-limiting examples of an artificial intelligence server 109 may include a workstation computer, a laptop computer, a server computer, a mobile device (e.g., smartphone, tablet), and the like.

The chatbot code may be stored in data records of a chatbot database 111, from which the artificial intelligence server 109 may query and retrieve certain chatbots. In operation, the artificial intelligence server 109 may receive instructions to execute a particular chatbot. The instructions from the customer device 117 may include a chatbot identifier data field that identifies which chatbot the artificial intelligence server 109 should retrieve from the chatbot database 111. In some cases, the chatbot code may contain variables that indicate expected types of data. The artificial intelligence server 109 may receive requisite variable data from the customer device 117 before and/or during execution of the chatbot. As mentioned, it should be appreciated that, in some embodiments, other devices of the digital therapy service 101, such as an operations server 103, may perform one or more of the processes described herein as being performed by the artificial intelligence server 109.

The artificial intelligence server 109 may have software that implements and/or executes a chatbot. In some cases, a chatbot may be its own software program; and in some cases, a chatbot may be a portion of a software program that instructs another executing program of the artificial intelligence server 109 how to function, or a logical or other machine-readable representation (e.g., a decision tree, UML, XML) that is implemented by software of the artificial intelligence server 109. Customers may interact with chatbots through chatbot interfaces, which may be presented to customers on GUI of the customer device 117. Outputs produced by chatbots may include presenting customers with, for example, text, videos, audio playback, audiovisual playback, and hyperlinks, among others. The outputs produced by a chatbot may be generated according to how the code of the chatbot is executed and interpreted by the artificial intelligence engines; particularly with respect to any inputs from the customer device 117 and/or variable data received from the customer device 117.

The digital therapy service 101 may comprise any number of service provider devices; an exemplary use of a service provider device may be as a coach computer 113. A service provider device, such as a coach computer 113, may be any computing device comprising a processor and machine-readable memory capable of executing the various processes described herein. Non-limiting examples of the service provider device may be a workstation computer, a laptop computer, a server, a mobile device (e.g., smartphone, tablet), and the like. A service provider device as described herein may be configured to for use and operation by a coach. However, a server provider device may be configured for various other personnel of the digital therapy provider, such as a health specialist and a system administrator, among others. As mentioned, although only a coach computer 113 is shown as an exemplary service provider device in FIG. 1, some embodiments may comprise multiple service provider devices configured with the functions and configurations needed by the various personnel.

In implementations where a service provider device may be configured as a coach computer 113, the coach computer 113 may have one or more GUIs that allow a coach to interact with the coach software and provide instructions to the coach computer 113, providing the coach with access to, for example, customer profiles, customers, and various other devices and features of the system 100. In some implementations, the coach may use the coach computer 113 to generate various data inputs for the operations server 103 to consume for particular processes or analyses, sometimes referred to as a "coach input." The coach computer 113 may also query and manage data about customers stored in a customer database 105. As an example, using a coach computer 113, a coach may submit a query to the customer database 105 to retrieve information about a particular customer. The data records of the customers may be organized by customer identifiers (IDs), and thus the appropriate data record may be retrieved according to the customer ID identified in the query. One skilled in the art would appreciate that search queries may be executed according to any number of keywords, data fields, or other search algorithms. The GUI of the coach computer 113 may present, in human-readable formats (e.g., text, images, audio), one or more data fields of the customer's data record retrieved from the customer database 105. In this example, the GUI may indicate a health condition (e.g., diabetes) that the customer wishes to address and related health and/or lifestyle information to educate the coach about the customer's current physical/health status and/or behaviors. The GUI of the coach computer 113 may then allow the coach to select components of a therapy regimen (e.g., exercise schedule, diet regimen, application interaction requirements), which the coach computer 113 may then transmit to the operations server 103. The operations server 103 may then generate the files and instructions to be transmitted to the mobile application of the customer device 117, may update the data record of the customer in the customer database 105 to include the parameters or requirements associated with the customer's therapy regimen.

A GUI of the coach computer may be organized as a dashboard or similar presentation that allows a coach to review the data of one or more customers under the coach's care. The software of the coach computer 113 may query the data of the customer's data record, and present the data in an organized GUI. The coach may use this dashboard GUI to, for example, review data for the status and progress of a customer's therapy regimen (e.g., health scores, milestones and achievement indicators, customer-inputted data), review updated data for the customer, and transmit data updates for the customer's data record, among other operations.

In some circumstances, the coach computer 113 may transmit to the operations server 103 and/or the customer database 105 an update to the customer's therapy regimen instructing the operations server 103 to include some additional task to be performed by the customer (e.g., generate summary of a telephone call with the coach, change to exercise regimen), or the coach computer 113 may update data in the data record for the customer such that triggers an automated response by the operations server 103 to identify an additional task that must be performed by the customer in the course of their therapy regimen. In such circumstances, when an additional task must be performed by the customer, the operations server 103 updates the customer database 105 to include information about the new task, but then the operations server 103 may also query an application database 107 to determine whether a chatbot should be implemented by the customer device 117 to provide the relevant instructions or information to the customer. When implementing the chatbot, the customer device 117 may send to an artificial intelligence server 109 a chatbot identifier and instructions to execute the chatbot corresponding to the chatbot identifier. In some embodiments, the operations server 103 may transmit the chatbot identifier and/or execution instructions directly to the artificial intelligence server 109. The output generated by the artificial intelligence server 109 may then be transmitted by the artificial intelligence server 109 directly to the customer device 117, or indirectly to the customer device 117 via the operations server 103.

For example, after a telephone call between the coach and the customer to discuss the therapy, the coach may use a GUI to update an ongoing coaching journal, where the data of the journal (e.g., text, audio, video) may be stored into the customer database 105. The operations server 103 may detect the update to the coaching journal in the customer's data record, and then automatically identify a chatbot identifier for a chatbot that prompts the user to input data for a customer journal. The operations server 103 may automatically update a chatbot queue of the customer in the customer database 105 to include the chatbot identifier, which the operations server 103 may then transmit to the customer device 117 at a predetermined time. It should be appreciated that, in some embodiments, the operations server 103 may transmit a chatbot directly to an artificial intelligence server 109 at a predetermined time. Additionally or alternatively, after the telephone call, the coach may use the GUI to manually update the therapy regimen to include a task for the customer to complete the customer journal update. The operations server 103 receives the update to therapy regimen, selects the appropriate chatbot identifier, and updates the chatbot queue of the customer.

In some implementations, a coach may use a coach computer 113 to communicate directly with a customer. For example, a coach computer 113 may generate and present a GUI that receives text or other types of data inputs from the coach and displays text or other types of data inputs that the coach computer 113 has received from the customer device 117. For instance, to receive text inputs, the software of the coach computer 113 may receive text-based inputs from, for example, a keyboard of the coach computer 113. The coach computer 113 may receive audio inputs from, for example, a microphone of the coach computer 113. The coach software may also query a file structure of the coach computer 113 or private network of the digital therapy service 101, such that the inputs are computer files stored on the coach computer or other device of the private network. Such computer file inputs may be transmitted to the customer device 117, where customer device 117 may then present aspects of the computer file (e.g., text, audio, video) to the customer via one or more GUIs. In this example involving a GUI of the coach computer 113, the coach and the customer may interact through a chat session, where each device (e.g., coach computer 113, customer device 117) generates and presents GUIs that display text, audio, and/or video of the chat. In some cases, a GUI of the coach computer 113 may present a dashboard interface that displays customer information, including health data (e.g. body metric measurements, health score), behavior data (e.g., number of customer interactions with the digital therapy service 101), and customer journal entries. The dashboard interface, or other interface, provided by the GUI may also display a timeline of events in a therapy regimen, and may present a history of chatbot provided to a customer and history of interactions, which may include transcripts and/or data files of chatbot-related exchanges.

In some cases, packets carrying the chat-data may be routed through an operations server 103 or either of the devices involved may forward the chat-data to the operations server 103, such that the operations server 103 may store the data inputs into the data record of the customer. The operations server 103 may also review the chat-data, using natural language processing or some other review processes and routines (e.g., parsing, tokenizing), to identify any potentially triggering events.

A customer device 117 may execute any number of software application programs, including, for example, a therapeutic software application program of the digital therapy service 101, where the therapeutic software allows the customer to interact with the services and features of the digital therapy service 101, and/or a third-party application associated with a third-party server 119. The customer device 117 may further exchange data and/or machine-executable instructions with, for example, an operations server 103 and an artificial intelligence server 109, via one or more networks 123. It should be appreciated that a customer device 117 may be any computing device comprising a processor and machine-readable memory capable of executing the processes and tasks described herein. Non-limiting examples of a customer device 117 may include a workstation computer, laptop computer, a server, a mobile device (e.g., smartphone, tablet), and the like. In operation, the customer device 117 may receive data and/or machine-executed instructions related to a customer's therapy regimen, and display and capture relevant data via one or more GUIs. A GUI may display directions to a customer so they may follow the customer's therapy regimen.

The customer device 117 may display one or more GUIs that operate as a chat interface, which may allow the customer to interact with a coach or any number of automated chatbots. In operation, the customer device 117 may receive a chatbot identifier from the operations server 103 via one or more networks 123 after a triggering event (e.g., customer accesses the chat interface) or after a predetermined interval. To implement a chatbot identified by the chatbot ID, the customer device 117 may transmit the chatbot identifier to an artificial intelligence server 109 as part of a request for the artificial intelligence server 109 to execute the chatbot identified by the chatbot identifier. In some cases, the chatbot to be executed consumes and uses certain data fields stored in a database of the digital therapy service 101, application server 115, third-party server 119, or other data source. The operations server 103 may query or otherwise collect this expected data and pass this data to the customer device 117 as variable data. In such cases, the customer device 117 may transmit this variable data as part of the request with the chatbot identifier. Additionally or alternatively, in real-time, the artificial intelligence server 109 may request variable data from the customer device 117, thereby instructing the customer device 117 to request this variable data from the operations server 103 accordingly. The artificial intelligence server 109 may, in some implementations, directly request variable data from the operations server 103. Additionally or alternatively, the artificial intelligence server 109 may directly request or otherwise receive variable data directly from an application server 115 and/or a third-party server 119.

In some embodiments, the customer device 117 may receive data from data contribution devices 121, such as smart home devices, wearable devices, and the like. The customer device 117 may receive such data through wired (e.g., USB®, FIREWIRE®, wired LAN) or wireless (e.g., BLUETOOTH®, WI-FI®) connections and then forward the data to the operations server 103. The customer device 117 may receive and transmit the data at a given interval, or the customer device 117 may transmit data to the operations server 103 in response to receiving the data from a data contribution device 121. In some instances, the customer device 117 may transmit data from a data contribution device 121 to a third-party server 119 associated with a particular data contribution device 121. For example, a data contribution device 121 may be a wearable device fitness tracker 121b (e.g., FITBIT®, GARMIN®). In this example, a third-party server 119 may operate a remote computing service (e.g., cloud or web-application) that collects and manages data captured and generated by the corresponding wearable device 121b. The customer device 117 may execute software for the third-party service that transmits the data to the third-party server 119, which may be remotely queried by the operations server 103; or the customer device 117 may directly transmit the data generated by the wearable device 121b to the operations server 103. The data may then be, for example, stored into the customer database 105, transmitted and/or presented to a coach computer 113 via a GUI, or trigger an action by the operations server 103.

As another example, a data contribution device 121 may be a smart scale 121a, which may be a type of "smart device" that electronically and/or automatically performs certain data-collection functions and then provides the data to a customer device 117. In this example, the smart scale 121a may be configured using an interface on the customer device 117, and may connect with the customer device 117 via Wi-Fi and/or Bluetooth®. When the customer steps onto the smart scale, the smart scale 121a may generate data indicating, for example, the customer's weight, and other possible measurements (e.g., BMI, hydration). This body measurement data may be transmitted to the customer device 117 and/or a third-party server 119, along with any number of additional data fields (e.g., timestamp), until such data is forwarded by the customer device 117 or third-party server 119 to the operations server 103. Additionally or alternatively, in some implementations, the operations server 103 or artificial intelligence server 109 may receive data directly from the smart scale 121a or other data contribution device 121.

Data contribution devices 121 may be devices functioning as data sources generating and providing data inputs to the digital therapy service 101. Non-limiting examples of a data contribution device 121 may include electronic body metric measurement devices (e.g., smart scale 121a, electronic sphygmomanometer, electronic blood glucose monitor, electronic cholesterol monitor), wearable devices (e.g., fitness trackers 121b), and the like. The data contribution devices 121 may generate data containing body measurement data (e.g., weight, A1C, HDL, CDL, blood pressure) in any number of formats and communicate the data to a customer device 117, third-party server 119, operations server 103, artificial intelligence server 109, or other device. The communication may be performed using any number of wired or wireless technologies (e.g., Ethernet, LAN, WI-FI®, BLUETOOTH®).

Therapy Regimen Execution

Figure 2A:
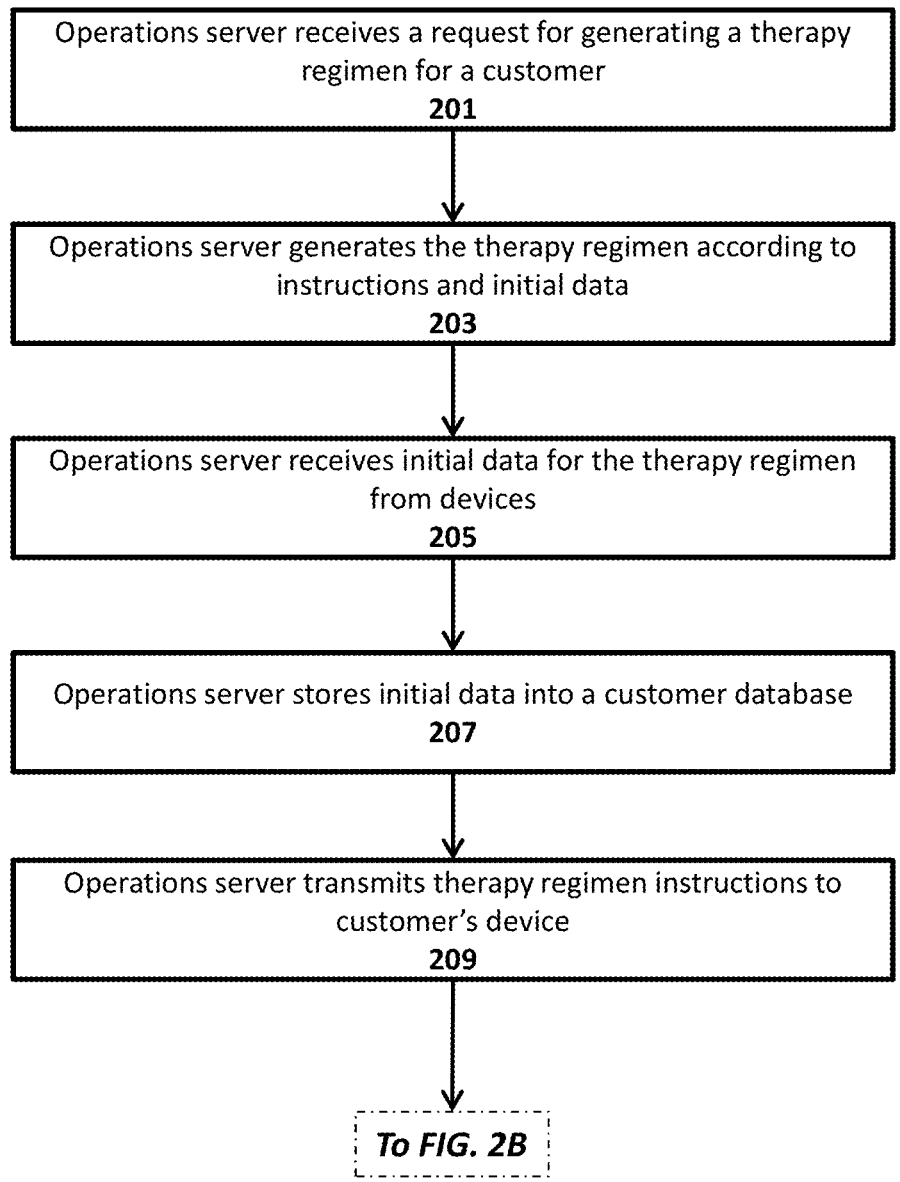
FIG. 2A and FIG. 2B show execution of a method for generating and monitoring a customer's therapy regimen, according to an exemplary embodiment.
Figure 2B:
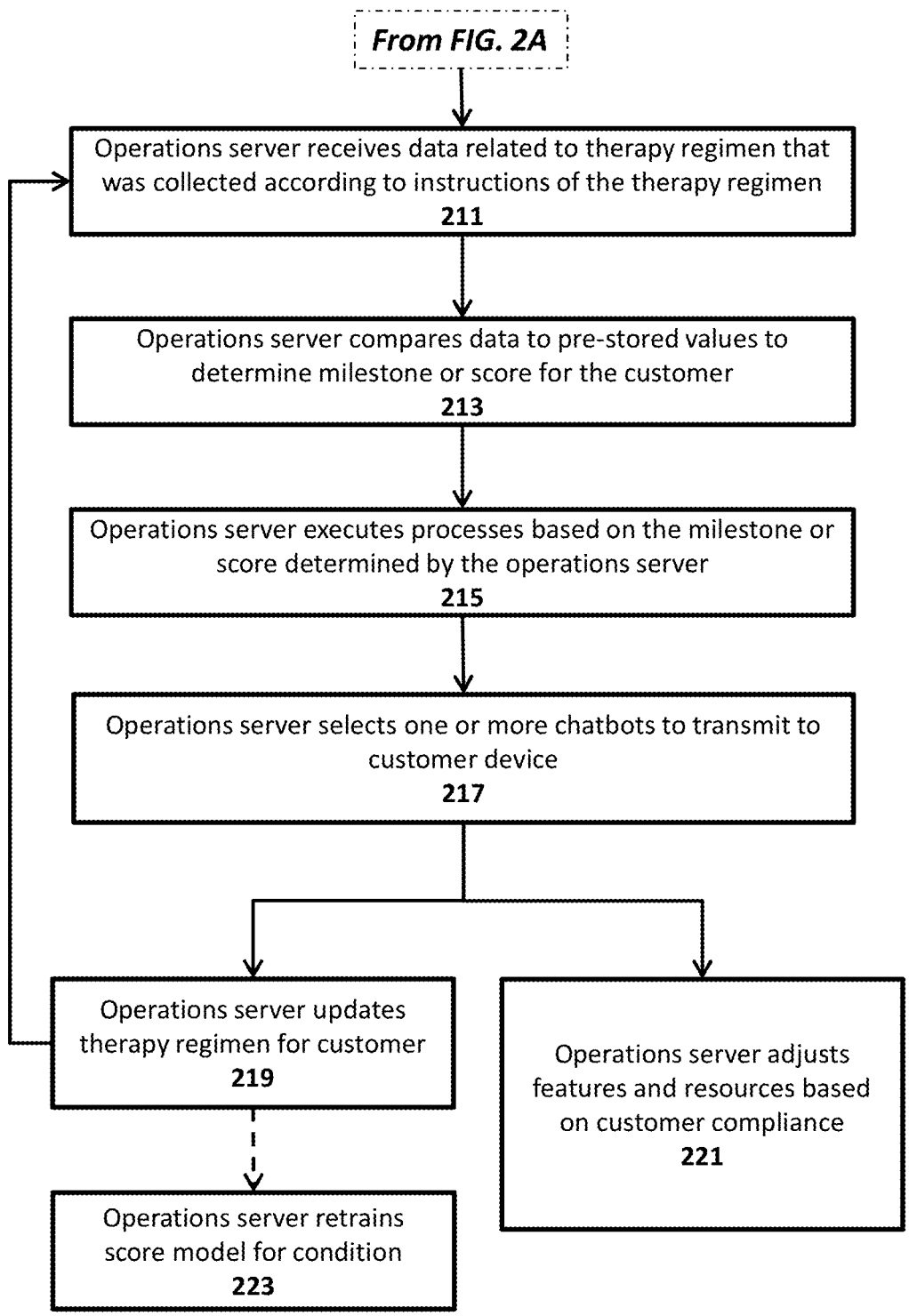

FIG. 2A and FIG. 2B show execution of a method 200 for generating and monitoring a customer's therapy regimen, according to an exemplary embodiment. The exemplary method 200 comprises steps 201, 203, 205, 207, 209, 211, 213, 215, 217, 219, 221, and 223. However, it should be appreciated that some embodiments may include additional or alternative steps, or may omit one or more steps, without departing from the scope of this disclosure. For ease of explanation, the exemplary method 200 is described as being executed by an operations server of a digital therapy service. However, one having skill in the art would appreciate that various steps may be executed in a distributed computing environment by any number of computing devices capable of executing such steps. Execution steps may be divided according to design decisions that determine an amount of processing is required by a client device (e.g., customer device, coach computer) as compared to other devices of the digital therapy service (e.g., operations server). As such, in some embodiments, certain steps described herein as being executed by an operations server, may be executed by, for example, a customer device. It can further be appreciated that each of the steps described herein could be logically broken into or viewed as comprising more than one sub-step or sub-component.

As shown in FIG. 2A, in step 201, an operations server may receive a request for generating a therapy regimen for a customer of a digital therapy provider, where the request may be received by the operations server from a coach computer, customer device, or any other computing device. The operations server may generate the request based on a health condition and/or data associated with the customer The request may trigger the operations server to identify a particular set of tasks (e.g., diet routine, exercise routine, coach call schedule) associated with the therapy regimen to be performed by a customer of a digital therapy provider. The request may comprise one or more data fields containing information that the operations server may use to construct the therapy regimen for the customer. The information of the request may include, for example, an indicator of a health condition (e.g., diabetes, high blood pressure, high cholesterol) or therapeutic goal of the user, and information related to the customer (e.g., customer name, customer identifier).

In some implementations, the operations server or other computing device may automatically generate a request for a therapy regimen based on certain prompting events identified by the operations server or other computing device. In some instances, the operations server may be triggered to generate the request in response to identifying a change to data stored in a database. For example, the operations server may detect a new data record for a new customer being created in the database. In this example, the operations server may query the new data record for the data needed for the request.

In some implementations, a user (e.g., customer, coach) may manually input the data for the request using a GUI of computing device. The operations server may receive the request from the user's computing device (e.g., customer device, coach computer). Software executed by the user's computing device may receive the data for the request through a GUI, which may be a web-browser or an interface native to a locally-installed software application. The user device may then generate the request with the inputted data and transmit the request to the operations server. For example, a customer device may generate and present a GUI to a new customer who is registering with the digital therapy service, where the GUI contains a number of input fields for accepting information about the new customer. After the customer has completed the input fields of the GUI (e.g., name field, condition field), the customer may input instructions for the customer device to transmit the data of the input fields to the operations server. As another example, a new customer may contact a coach of the digital therapy service over the telephone or other communications means (e.g., SKYPE®), where the coach may then perform an intake interview for the new customer. In this example, coach computer may generate and present a GUI to the coach who is inputting data for the new customer, where the GUI contains a number of input fields for accepting information about the new customer. After the coach has completed the input fields of the GUI (e.g., name field, condition field), the coach may input instructions for the coach computer to transmit the data of the input fields to the operations server.

In step 203, the operations server may generate the therapy regimen according to the data of a request, which in some cases, may include initial data related to the customer as received by the operations server. As mentioned, a therapy regimen may be a collection of tasks to be performed by the user (e.g., diet, exercise routine, schedule of telephone calls with coach), where the therapy regimen may be embodied as any number of machine-readable code and/or machine-readable computer files containing instructions and data to be executed and accessed by various computing devices, such as an operations server, a customer device, and a coach computer, among others. For example, a therapy regimen may instruct an operations server to include a predetermined set of one or more chatbots for the customer device to implement with an artificial intelligence sever. As another example, a therapy regimen may indicate to the operations server which GUIs to provide to the customer device, and, likewise, the therapy regimen code instructs the customer device to collect certain data at a certain frequency. As yet another example, the therapy regimen may indicate to the operations server one or more threshold values and/or milestones that the operations server may use to measure the customer's progress, or that the operations server may transmit to the customer device to be displayed on a GUI. In some implementations, an application database may store certain data or machine-executable code for therapy regimens that address certain conditions. It should be appreciated that, in such case, generating the therapy regimen may comprise the operations server selecting data or code comprising the therapy regimen addressing the particular health condition for the customer.

The therapy regimen may be generated according to a health condition of the user, and may be associated with certain parameters that correspond to data fields or expected types of data, such as descriptive information (e.g., age, gender), body metric measurements (e.g., weight), and others. Additional or alternative examples of body metric measurements may include lipid profile, cholesterol level, triglyceride levels, low-density lipoprotein level, high-density lipoprotein level, very low-density lipoprotein level, blood pressure, fasting blood glucose level, blood insulin level, fasting insulin level, alanine transaminase level, blood GIP level, insulin resistance, or glycated hemoglobin (HbA1c) level. In some cases, the request received at step 201 may contain all or some of the data that the operations server uses to generate the therapy regimen. And, in some cases, the request may indicate the requisite data fields and databases that the operations server should query for the data needed for the operations server to generate the therapy regimen. For example, a request may contain a customer identifier corresponding to a database record for the customer, and an indicator of the condition that the customer would like to address. While generating the therapy regimen for the condition, the operations server may query a customer database for the customer's data record corresponding to the customer identifier in the request. The operations server may then use the data retrieved from data fields (e.g., age, gender) indicated by the request to generate the therapy regimen.

In some implementations, the therapy regimen may provide a customer access to certain therapeutic features, where the therapeutic features may be machine-executable routines/processes of the digital therapy service, such as chatbots, personalized coach calls/interfaces of various types (e.g., text, audio, visual), health scores, and milestone determinations, among others. The therapy regimen may indicate to the operations server which features a customer's authentication credentials or the customer device should have access to, and the operations server may activate such features on behalf of the customer (e.g., grant customer credentials or customer device access to such features).

In an optional step 205, the operations server may receive initial data for the customer from any number of devices, to the extent that any such data may not have been received in steps 201 or 203. The initial data may include any number of body metric measurements of the customer, and may include data relevant to the health condition addressed by the therapy regimen (e.g., height, weight, blood pressure, blood sugar, cholesterol). In some cases, such as the exemplary method 200, the initial data to be collected is agnostic to the parameters of the therapy regimen. In this way, more data is available to the operations server when executing various processes, and a more complete picture of the customer's health is available to the coach and any specialist. In such implementations, the customer device is instructed to present a GUI displaying an output tasking the customer with collecting or inputting the initial data. And in some cases, the initial data to be collected may be based on the therapy regimen or by the condition. In such cases, the initial data may include certain data fields that are indicated as parameters for the therapy regimen or the condition.

The devices that collect and transmit the initial data to the operations server may be any computing device capable of capturing the initial data. Non-limiting examples of such devices may include customer devices (e.g., computer, mobile device), service provider devices (e.g., coach computer, specialist computer), smart home devices (e.g., electronic scale, smart appliances), electronic body metric devices (e.g., sphygmomanometer, blood glucose meter, cholesterol testing device), wearable devices, fitness trackers, and the like. In some instances, the data may be inputted by a user directly into a GUI of a computing device that may forward the inputted data to the operations server. And, in some instances, a data contribution device may generate data that is transmitted to a customer device, which, in turn, forwards the data to the operations server. As an example, a customer or coach may input the initial data into data fields of a GUI of a customer device or coach computer. The customer device or the coach computer may then transmit the initial data received by the GUI to the operations server. As another example, a customer may step onto a smart scale that may generate data for certain body metric measurements (e.g., weight, BMI), which the smart scale may then generate to a customer device using any number of data communications protocols (e.g., WI-FI®, BLUETOOTH®, infrared). In this example, the customer device may then transmit this data from the smart scale to the operations server as initial data.

In step 207, the operations server stores data that may have been received in any of steps 201, 203, and/or 205 into a customer database. The customer database may contain a database record for each customer in the system. As the operations server receives data inputs, such as the initial data, the operations server may update the record of the customer to include the data received from the various devices. As mentioned, the customer's data record may also include data associated with the therapy regimen, including tasks assigned to them and task-related data (e.g., diet, shopping list, exercise routine, journal entries, calendar of events, scores, milestones). In some implementations, data records of customers may also include a chatbot queue, which may contain one or more chatbot identifiers for the operations server to transmit to the customer device for implementation.

In step 209, the operations server may transmit certain therapy regimen instructions to the customer device. The instructions may be machine-executable code that instructs the customer device to execute any number of processes, and/or the instructions may include pointers and/or identifiers directing the customer device to execute machine-executable code stored on the customer device. For example, the customer device may be instructed to transmit various types of data to the operations server. In some cases, to collect the data required by the instructions, the customer device may present a GUI that prompts the customer to input the data into corresponding fields of the GUI. And in some cases, the customer device may poll or otherwise receive data from various devices configured to generate the data required by the instructions. As another example, the customer device may receive a chatbot identifier with instructions to implement a chatbot corresponding to the chatbot identifier. The customer device may then be triggered to transmit, to an artificial intelligence server, a request for the artificial intelligence server to execute the chatbot corresponding to the chatbot identifier.

Description of exemplary method 200 continues as shown in FIG. 2B.

In step 211, the operations server receives data related to the therapy regimen from one or more devices (e.g., customer device, data contribution devices) that have collected and/or generated such data. The data may include any number of body metric measurements of the customer, and may include data relevant to the health condition addressed by the therapy regimen (e.g., height, weight, blood pressure, blood sugar, cholesterol). Additionally or alternative, the data may include additional information related to a task performed by a customer, coach, or other user, and/or information related to the therapy regimen overall.

For example, the data may include text or audio input of a customer or coach's journal entry, which may be a summary of a recent telephone call or reflection on the therapy regimen. Such data is intended to be inputted by a customer through a GUI not only for the therapeutic purposes of monitoring the customer's experience, but also as a means of tracking the user's interaction and effort-level. Accordingly, the very entry of such a journal entry may be tracked as a data field, in addition to the actual data of the journal entry. In some cases, the software of the customer device may include with the data an indication of an interaction between the customer and the software application. In some cases, the operations server may identify types of data that are generated according to a customer's manual input, such as a journal entry, data inputted during a chatbot session, detecting a completion status of certain chatbots in the customer's chatbot queue, where such data that was generated according to the customer's manual inputs may be indicators of interactions. The operations server may receive the indicator of interactions as part of the data and may track an amount of interactions between the user and the mobile application. This may be particularly useful in circumstances where the therapy regimen of the customer requires a customer to have a certain amount of interaction with the software application. The operations server may update the customer database records to include indicators of customer interactions with the therapeutic software running on the customer device, software running on the operations server, and/or software running on the artificial intelligence server; and, in some cases, the operations server may use the indicators of interaction to determine, for example, a customer's health score or milestone, in accordance with the therapy regimen. Other non-limiting examples of data may include one or more of the following: whether a meal plan was followed; whether a lifestyle regimen activity was completed; whether a coaching call was completed; whether one or more, or all, ingredients on a shopping list were procured; whether the subject consumed a specified amount of water or whether the subject consumed water; a number of meal plan meals consumed, a number of activities completed, a total number of calories burned in one or more activities, a number of coaching calls completed, length of one or more coaching calls, a number or fraction of ingredients procured from a shopping list, a number of hydration events, or a total volume of hydration. In some cases, where a meal plan was not followed, the data can include whether a meal fallback was consumed. In some cases, data can include type of, e.g., physical, activity completed. In some cases, data can include number or frequency of body weight measurements performed.

As another example, the customer device may prompt the customer to input data, such as body metric measurements or other inputs, or may poll such data from various external data contribution devices (e.g., FITBIT®) or software applications on the customer device (e.g., FITBIT® application). The customer device may transmit the data to the operations server at a predetermined interval or as the data is received, according to the therapy regimen. It should be appreciated that devices that collect and transmit the data to the customer device or operations server may be any computing device capable of capturing the data. Non-limiting examples of such devices may include customer devices (e.g., computer, mobile device), service provider devices (e.g., coach computer, specialist computer), smart home devices (e.g., electronic scale, smart appliances), electronic body metric measurement devices (e.g., sphygmomanometer, blood glucose meter, cholesterol testing device), wearable devices, fitness trackers, and the like.

As mentioned, in some cases, the data may be inputted by a user directly into a GUI of a computing device that may forward the data to the operations server. For instance, a customer or coach may input data into data fields of a GUI of a customer device or coach computer. The customer device or the coach computer may then transmit the data received through the GUI to the operations server. Additionally or alternatively, in some cases, one or more data contribution devices may generate and transmit data to a customer device, which, in turn, forwards the data to the operations server. For example, a customer may step onto a smart scale that may generate data for certain body metric measurements (e.g., weight, BMI), which the smart scale may then generate and transmit to a customer device using any number of data communications protocols (e.g., WI-FI®, BLUETOOTH®, infrared). The customer device may then transmit this data from the smart scale to the operations server.

In step 213, the operations server may determine a milestone and/or score. The operations server compares data of the customer data record to corresponding pre-stored values to determine milestone achievements and/or scores for the customer. As mentioned, a customer database record may contain any number of data fields that may be populated with data received from, for example, a customer device. The values of these data fields are expected types of data, such as a "customer name" field that contains text data where the value of the text data is a customer's name. Therapy regimens and/or health conditions may be associated with certain parameters that are used to develop aspects of a therapy regimen and to track customer progress, where the parameters correspond to certain data fields. More specifically, the therapy regimen of a customer may indicate the relevant parameters to the operations server, where the parameters of the therapy regimen and/or health condition correspond to data fields that the operations server should reference when monitoring customer therapies (e.g., determining a health score, training a health score model, determining customer progress through the therapy regimen, determining the status of the therapy regimen).

Continuing with step 213, the operations server may query certain data fields of the customer data record to determine the customer's progress. At a predetermined interval or in response to a particular event (e.g. receiving updated data about a customer), the operations server may determine the parameters of the therapy regimen that are relevant to the condition of the user. This may be indicated by data fields in the customer database and/or in data fields of an application database of the digital therapy service that stores data records for particular therapy regimens or conditions. The same or different database may further contain scoring data records that the operations server may use to determine a milestone achievement for the customer. For instance, a blood glucose data field of a scoring record may contain a pre-stored A1C value, which the operations server may compare against a current A1C value in a blood glucose data field or other data field of the customer record containing the blood glucose data. Moreover, the same or different database may additionally or alternatively contain scoring data records that the operations server may use to determine a health score for the customer. The data fields of these records may include, for example, scoring models for conditions and threshold indicators for the health scores. For instance, the operations server may identify a scoring record containing a health score model that corresponds to the condition of the customer (e.g., diabetes), where the scoring record indicates the expected data fields of the health score model (e.g., A1C value, weight value). The scoring record may further indicate a threshold value corresponding to the health score model, such that the threshold value may benchmark the resulting health score calculated by the operations server for the customer using the health score model.

In some implementations, scoring records may contain multiple threshold values, which may function as, for example, upper and lower threshold bounds for expected performance. In such implementations, the operations server may determine whether parameter values in the customer data record relevant to the customer's condition and therapy regimen are above, below, or within expectations. Such granular classification for the customer facilitates a wider range of potential functions to be performed by the operations server. For instance, the operations server may determine that values of a customer's data record or their calculated health score is below a lower-bound threshold, and thus the customer is non-compliant. This may trigger the operations server to, for example, identify a new chatbot to be implemented and then update the customer's chatbot queue, update the customer's therapy regimen (e.g., adjust diet, adjust exercise, increase number of coach calls, increase the number of tasks requiring customer interactions), or discontinue the customer's therapy regimen, among others.

In some implementations, the threshold values and/or the health score model applied by the operations server may be based on any number additional variables, such as when the operations server applies a threshold value and/or health score model or the customer's history of the relevant values. For instance, the threshold values for a blood glucose data field may be increasingly lower as time progresses, or the operations server may select a different health score models to apply as time progresses. In this way, the operations server is determining whether the customer met an achievement milestone or calculating the customer's health score based on comparisons with data values and/or statistics that were culled and generated from records of similarly situated customers, which provide the basis for the expectations. Additionally or alternatively, the threshold values and/or health score models may be applied based, at least in part, with consideration of the history of data values in the customer's data record. For example, the operations server may identify and select more manageable threshold values to apply against the customer's data when the initial inputs are much higher.

In some implementations, using a GUI of a coach computer, a coach may manually input threshold values and/or select a health score model to apply. The inputted threshold value and/or selected health score model may be stored into the customer data record. Additionally or alternatively, in some cases, the inputted threshold value and/or selected health score model may be stored in one or more databases of the digital therapy service. In such cases, one or more identifier values may inputted into the customer data record that may instruct the operations server where to find the coach-selected threshold values and/or health score model.

In step 215, the operations server executes processes based on the milestone or score. As mentioned, the operations server may be pre-programmed, or otherwise instructed by code of the therapy regimen, to execute any number of processes based on the determination of step 213. For instance, the operations server may generate instructions for the customer device to display an achievement interface via the GUI of the customer device, when the operations server determines that a particular value in the customer data satisfies a corresponding milestone threshold value. The achievement interface may be configured to display a congratulatory message and additional data queried or generated by the operations server (e.g., date/time, customer's data value, threshold data value). In some cases, the achievement GUI may also display an average or other statistically-determined value that corresponds to the data field of the tested customer value and that represents a similarly-situation cohort of customer records.

In some implementations, the operations server may update a chatbot queue for the customer based on the determination of step 213. The operations server may determine that a particular chatbot should be implemented by the customer device as a result of the milestone or score. The operations server may identify the chatbot identifiers for the chatbots to be implemented and then include those chatbot identifiers to the chatbot queue for the customer. For instance, the health score of the customer may fail to satisfy a lower-bound threshold value. In response, the operations server may identify the chatbot identifiers for a chatbot that may, for example, report the calculated health score to the customer via a GUI of the customer device and then prompt the customer to input data of any type containing a reflection, and a chatbot that may, for example, interact with the customer to schedule a time to conduct a call with a coach.

In step 217, the operations server may select one or more chatbots to transmit to the customer device. The operations server may execute various processes in response to inputs received from various devices, and/or in response to one or more determinations (e.g., milestone achieve, health score) from step 213. In some circumstances, the action triggered for the operations server may include determining that one or more chatbots should be implemented by a customer device. In these circumstances, the executable code that triggered the need for the chatbot may contain chatbot identifiers corresponding to each of the chatbots. The operations server may then update the chatbot queue of the customer to include the one or more chatbot identifiers. The operations server may transmit the chatbot identifiers to the customer device, which may, in turn, transmit the chatbot identifier to an artificial intelligence server for execution. It should be appreciated that, in some implementations, rather than simply sending a chatbot identifier, the operations server may transmit the chatbot itself to the customer device, in addition to or as an alternative to the chatbot identifier.

In some implementations, the operations server may transmit data with the chatbot identifier to the customer device. In such implementations, the code of a chatbot may contain variables that expect certain data types during execution. The operations server may transmit this data to the customer device with the chatbot identifier, and the customer device may subsequently transmit this data to the artificial intelligence server. In some cases, the executable code that triggered the need for the chatbot may indicate to the operations server which data fields and/or which databases should be queried. Additionally or alternatively, in some cases, a database of the digital therapy service may indicate to the operations server which data fields and/or which databases should queried. It should be noted that the data expected by variables of the chatbot does not have to be transmitted to customer device at the same time as the chatbot identifier. The operations server may transmit the expected data in response to a request from the customer device. That is, the customer device may request the expected data from the operations server in real-time, while the artificial intelligence server is executing the chatbot.

In optional step 219, the operations server may update the therapy regimen of the customer. As mentioned, the operations server may receive data from the customer device related to the therapy regimen, which the operations server may use to execute any number of processes and outputs, such as updating a customer database record, outputting to a GUI of a coach interface, and generating one or more scores or milestone determinations, among others. In some implementations, the data may be used to manually or automatically update the therapy regimen of the customer.

As an example, using a coach computer a coach may review a GUI output of the data of a customer, and determine that therapy regimen should be adjusted, which may include, for example, changing threshold values, adjusting the required tasks for the customer to perform (e.g., diet, exercise, journal entries), and updating the chatbot queue of the customer to add, remove, or replace one or more chatbot identifiers.

As another example, the operations server may automatically update the therapy regimen in response to determining that, for example, a weight data value in the customer data has not satisfied an upper-bound threshold value for weight. In response, the operations server may update the therapy regimen by adjusting the tasks for the customer complete, which may include, for example, adjusting the customer's diet to include food with fewer sugars if the data value which failed the threshold was the customer's weight or A1C measurement.

The exemplary method 200 may thereafter execute in iterations, starting each iteration at step 211 until the customer completes the therapy regimen. It should be appreciated that other embodiments may iteratively execute starting at any step. Moreover, the operations server may be configured to determine a particular step or process to be executed when starting a successive iteration. For example, if the therapy regimen was updated by GUI inputs or by the operations server when executing step 215, then the operations server may start execution of the next iteration at step 209 by transmitting the therapy regimen to the customer device. In addition, it should be appreciated that nothing in this description should be construed as requiring a particular order to the execution of steps. The order of execution may vary by embodiment, and/or the order of execution may vary based upon inputs or interactions between users and devices of the system. For example, the operations server may check the select chatbots for execution earlier than as described in the exemplary method 200, according to the instructions of the therapy regimen.

In an optional step 221, the operations server may adjust features and/or resources provided to the customer and/or the therapeutic software application on the customer device based on the customer's health score, certain body measurement scores in the customer profile record, and/or achievement milestone comparisons. Features may include the operations of the computing components of the digital therapy service, such as the therapeutic software application of the customer device and the chatbots assigned to the customer, among other computer related functions. Resources may include other aspects of the digital therapy service that may be provided to customers during the course of treatment, such as additional coaches or more/less time with the customer's assigned coach, meeting time with specialist personnel (e.g., doctors, dieticians, nutritionists, psychiatrists/psychologists, kinesiologists, personal trainers), and other resources. For example, a customer may fail to satisfy one or more thresholds over a certain predetermined period, which may put the customer in a status of non-compliance, or the customer may satisfy one or more thresholds over a certain predetermined period, which may put the customer in a status excelling beyond compliance. In some cases, the therapeutic benefits of the systems and methods disclosed herein over the art are derived from the customer's regular and cooperative interactions with features of the software; a customer profile data record may contain one or more data fields containing data indicating a number of interactions between the customer and the therapeutic software application, coach, or other aspect of the digital therapy service. In this example, the operations server may determine that the customer may have too few interactions or more than required based on a comparison of the customer's amount of interactions and thresholds for the number of interactions, and thus according to the customer's therapy regimen, it may be necessary in some cases to tailor the resources and/or features for the treatment for the customer. As such, the operations server may automatically execute processes to, for example, add a scheduling chatbot to the customer's chatbot queue to increase or decrease a number of coach calls, adjust the customer's diet routine and/or exercise routine, increase or decrease the number of interactions that are required by the customer by adjusting the threshold and reporting that change to a customer via an interface, among other potential adjustments to the features and/or resources provided to the customer. Additionally or alternatively, the operations server may adjust the resources and/or features provided to the customer and/or the therapeutic software application of the customer device for the customer's treatment when data values or health score of the customer fail to satisfy a threshold or exceed a threshold by an amount that is greater than some predetermined difference.

In effect, in optional step 221, the operations server may automatically adjust the features and/or resources assigned to a customer and/or the customer's therapeutic software application, such that the operations server may automatically adapt the customer therapy regimen to suit the customer's needs. If the operations server determines that the customer's scores, data fields, and/or milestone determinations indicate that the customer is doing better than expected, according to baseline parameter comparisons, then the operations server may adjust the features and/or resources to, for example, require less oversight or allow for more leeway in behavior. In some cases, this may beneficially allow the operations server and the digital therapy service to allocate resources to customers in greater need. Likewise, if the operations server determines that the customer's scores, data fields, and/or milestone determinations indicate that the customer is lagging behind expectations, according to baseline parameter comparisons, then the operations server may adjust the features and/or resources to, for example, require more meetings with one or more coaches and/or specialists and require more interactive activities (e.g., more dietary journal entries, more exercise journal entries). In some instances, the operations server may implement such adjustments by, for example, adding or removing certain chatbots from the customer's chatbot queue, or adjusting the threshold requirements used by the operations server to determine the customer's progress, health scores, and/or milestone achievements.

In an optional step 223, the operations server may retrain a health score model applied for the customer's condition. As mentioned, the health score model may be a statistical model that is trained according to, for example, inputs from an administrator computer or an updated data records of other customers that retrains aspects of the health score model, such as weights assigned to certain parameters, where the labeled data set may be a computer file containing data records having pre-determined values or metadata that are associated with relevant data fields. When retraining a health score model, the operations server may perform any number of statistical and/or regression algorithms on updated values of data fields ingested by the health score model and/or additional inputs from an administrator computer or database. At a predetermined interval of time or at a triggering event, the operations server may use one or more data fields from any number of customer records for customers having, for example, the same condition and/or the same or similar therapy regimen, among other possible criteria. The predetermined interval may be any amount of time. The triggering event may be any change to the data stored in the databases that the operations server may query or otherwise detect and subsequently execute the retraining processes. For example, the triggering event may be the operations server determining that a predetermined number of customers have completed therapy regimens for a given condition, or the triggering event may include the operations server determining that a predetermined number of new customers have participated in therapy regimens for a given condition for a predetermined time (e.g., 50 new customers have participated for 6 weeks).

Chatbot and Chatbot Queue

Figure 3:
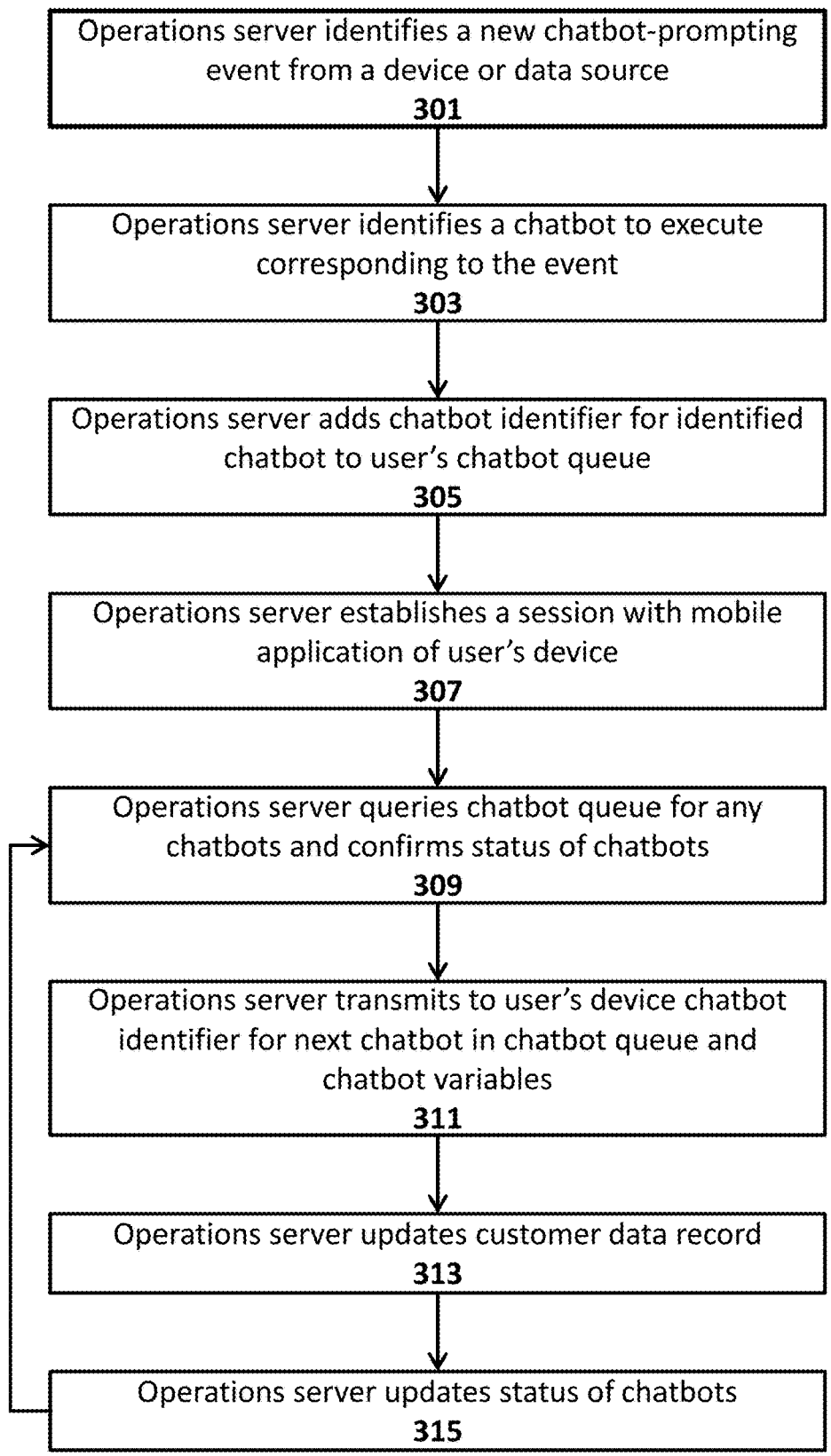
FIG. 3 shows execution of a method for generating and updating a chat bot queue by an operations server, according to an exemplary embodiment.

FIG. 3 shows execution of a method 300 for generating and updating a chatbot queue by an operations server. The exemplary method 300 comprises steps 301, 303, 305, 307, 309, 311, 313, and 315. However, it should be appreciated that some embodiments may include additional or alternative steps, or may omit one or more steps, without departing from the scope of this disclosure. For ease of explanation, the exemplary method 300 is described as being executed by certain devices of a digital therapy service (e.g., an operations server, an artificial intelligence server). However, one having skill in the art would appreciate that various steps may be executed in a distributed computing environment by any number of computing devices capable of executing such steps. Execution steps may be divided according to design decisions that determine an amount of processing is required by a client device (e.g., customer device, coach computer) as compared to other devices of the digital therapy service (e.g., operations server). As such, in some embodiments, certain steps described herein as being executed by an operations server, may be executed by, for example, a customer device. It can further be appreciated that each of the steps described herein could be logically broken into or viewed as sub-steps or sub-components of the steps mentioned.

In step 301, an operations server identifies a new chatbot-prompting event based on data or instructions received from a computing device or data source. As mentioned, in some embodiments, an operations server may add chatbots to a customer's chatbot queue, the chatbot or chatbot identifier may be transmitted to a customer device for implementation, and the customer device may transmit the chatbot or chatbot identifier to an artificial intelligence server with instructions to execute the chatbot, and the artificial intelligence server may execute the chatbot. In some cases, the operations server may receive requests for chatbots from any number data sources, such as a customer computer or a coach computer. And in some cases, the operations server may dynamically generate requests for chatbots in response to the operations server identifying certain triggering events, according to software code executed by the operations server.

As an example, after a telephone call with a coach, the coach may enter a summary of the call into a field of a GUI displayed at the coach computer. When the coach submits the data containing the summary (e.g., text, computer file, audio, video), the coach computer submits the summary to the operations server. The coach computer may generate a request for a coach summary chatbot to be implemented. Alternatively, the operations server may automatically identify that incoming coach summary data was received and generate the request for the coach summary chatbot accordingly.

In step 303, the operations server identifies a chatbot to execute based on the identified event. Based on the code or instructions that prompted the request for a chatbot, the operations server may determine which chatbot should be implemented. As part of processing requests for chatbots, the operations server may determine a chatbot identifier for the chatbot. In some cases, where a customer or coach inputs a request for a chatbot using a GUI of a customer device or coach computer, the request received from the customer device or coach computer may contain a chatbot identifier. In cases where software code of the operations server triggered the need for a particular chatbot, the software code may also contain the chatbot identifier corresponding to the triggered chatbot.

In step 305, the operations server adds a chatbot identifier to a customer's chatbot queue. In the exemplary method 300, each of the data records in a chatbot queue of a customer may be associated with the particular chatbot, and each of the chatbot data records may include data fields used for implementing the chatbots, such as the chatbot identifier, a chatbot status indicator, and an indication of the data variables expected by the chatbot during execution. Although certain exemplary embodiments described herein mention that the operations server adds a chatbot identifier to a chatbot queue, it should be appreciated that, in some embodiments, the operations server may add a chatbot to a chatbot queue. More specifically, because a chatbot may be a computer file that comprises machine-readable data and/or machine-executable code, the operations server may add the chatbot (e.g., computer file, data, code) to the customer's chatbot queue in addition to or as an alternative to adding a corresponding chatbot identifier.

In an optional step 307, the operations server establishes a session with the therapeutic software application running on the customer device. The therapeutic software application of the customer device may have a number of features, including a chatbot interface. When a customer activates a chatbot interface feature of the therapeutic software application, the artificial intelligence server and customer device may establish a chatbot session. The establishment of this chatbot session may trigger the customer device, the artificial intelligence server, and/or the operations server to collect certain data inputs (e.g., an indication of interaction between the customer and the therapeutic software application). The establishment of the chatbot session may also trigger the operations server to query the customer's chatbot queue.

As described in the exemplary method 300, the operations server may transmit instructions for the customer device to implement a chatbot during an ongoing chatbot session. However, in some implementations, the chatbot instructions may be sent to the customer device for execution at any time, according to the software code of the operations device. For example, the operations server may determine that a reminder chatbot should be executed at a regular interval. The operations server may add one or more chatbot identifiers for a reminder chatbot to the chatbot queue at the beginning of the day. The operations server may then transmit each chatbot identifiers to the customer device at predetermined times of the day. In some instances, the customer device may transmit the chatbot identifier or chatbot with a push notification, which may be presented to the customer via a GUI according the operating system of the customer device. In this example, the operations server does not require a chatbot session to be established with the customer device before sending the chatbot identifier for the reminder chatbot.

In step 309, the operations server may query the chatbot queue of the customer for queued chatbots and confirms the status of any queued chatbots. As mentioned, the data records for chatbots in the chatbot queue may comprise a data field containing an indicator that indicates the status for the particular chatbot. Example of possible chatbot statuses may include:

A ready status—The chatbot is ready to be dispatched to the customer device. The operations server sends each ready chatbot one at a time ordered according to a particular queuing algorithm, such as first-in-first-out.

A dispatched status—The chatbot has been transmitted to the software application of the customer device. At this point, the software application has not displayed the first message of the chatbot to the customer.

A started status—The artificial intelligence server has begun executing the chatbot, and the software application has started displaying messages of the chatbot to the customer via chat interface presented on the customer device. The customer device and/or the artificial intelligence server may transmit a message to the operations server indicating that the artificial intelligence server has begun execution.

A completed status—The artificial intelligence server and the customer device have completed execution of the chatbot.

An invalid status—The chatbot is invalid. The operations server performs a check before dispatching the chatbot to confirm that the chatbot is still valid. For example, immediately before dispatching a Logging Bot to the customer device, the operations server may check the customer data record in the database to determine whether the customer still has meals to log, based on null or missing data for those particular data fields. If the operations server determines that the data fields corresponding to the meals log are populated, the operations server updates the status of the chatbot as invalid and, thus, the chatbot is not dispatched.

An expired status—Each chatbot has a specified expiration time. The operations server may automatically update the status of any expired chatbot. Many chatbots never expire, while some chatbot expire in 60 minutes or some other predetermined expiration time.

A deleted status—The chatbot has been manually deleted by an administrator, coach, or other personnel of digital therapy service.

In step 311, the operations server may transmit the next chatbot or the chatbot identifier for the next chatbot to the customer device. In some cases, the data record for the chatbot may indicate that a number of variables are expected by the software code of the chatbot. In such cases, the operations server may query databases for the data indicated in the chatbot's list of variables. The operations server may then transmit the required variable data, along with the chatbot identifier, to the customer device. Additionally or alternatively, in some cases, the operations server may respond to requests for variable data that are received from the customer device in real-time. In such cases, a chatbot may require data from a particular data field during execution. The artificial intelligence server may transmit a request for the data field to the customer device, and the customer device may then forward the request to the operations server. The operations server may query and return the requested data to the customer device, which may then forward the data to the artificial intelligence server.

Notably, the customer device may have all or some of the data requested by the artificial intelligence server stored locally, in which case the customer device may immediately respond to the request from the artificial intelligence server. Otherwise, the customer device may forward requests to the operations server.

As mentioned, the operations server may transmit the chatbot identifier of the next chatbot as determined by the operations server in step 309, and variable data identified as being required for the next chatbot. The operations server may select the next chatbot to be implemented by the chatbot according to any number of queuing procedures (e.g., FIFO, LIFO) or predetermined prioritization schemas. Additionally or alternatively, the operations server may select the next chatbot based on status indicators. Once selected, the operations server may transmit the chatbot identifier and related variable data to the customer device. The operations server may also update the status of the chatbot to indicate the chatbot was sent to the customer device (e.g., dispatched).

In step 313, the operations server may update the data record for the customer, based on execution of the chatbot. The operations server may receive data inputs (e.g., (journal entries, body metric measurements, indicator of interactions) from a customer device during or after chatbot execution. For example, the customer device may be instructed to implement a Logging Bot, and thus receives a chatbot identifier corresponding to the Logging Bot and/or data or code of the Logging Bot. The customer device may transmit the chatbot identifier or the chatbot to the artificial intelligence server for execution. The Logging Bot may be configured to accept inputted data regarding certain tasks or behaviors performed by the customer (e.g., meal logs, exercise log). When this data is inputted into the chat interface GUI of the customer device, the customer device may transmit the data to the artificial intelligence server to continue execution of the chatbot, and also to the operations server. The operations server may then save this data into appropriate data fields of the customer data record. As another example, in some circumstances, the operations server may be prompted to update a health score of the customer based on inputs received during execution of the chatbot. The operations server may update the customer data record to reflect the updated health score. Additionally or alternatively, in some implementations, the operations server may also receive data inputs directly from the artificial intelligence server, during or after execution of the chatbot.

In some cases, the data inputs from the customer device may also include updates to the status of the chatbot. For instance, while the artificial intelligence server is executing a chatbot, the customer device may transmit a status update for the chatbot to the operations server. The operations server may, in turn, update the customer's chatbot queue accordingly.

In step 315, the operations server updates the status of chatbots in the chatbot queue. After executing a particular chatbot, the operations server may update the chatbot's data record in the customer's chatbot queue. The update may change a status indicator field to indicate that the chatbot has been completed.

As mentioned, other possible statuses are possible as well. The operations server may update the status of chatbots according to any number of triggering events or at a given interval. For example, the operations server may update the status of a chatbot when a status update message has been received. As another example, the operations server may update the status of the chatbot when the operations server detects that an expiration time has expired. Additionally or alternatively, the operations server may update the status indicators for chatbots when the operations server conducts a check that is prompted by establishing a chat session with a customer device.

The exemplary method 300 may execute in iterations, starting each successive iteration at step 309, until, for example, the customer ends a chat session, the customer closes the software application, or the operations server determines there are no further chatbots to be implemented in the customer's chatbot queue. It should be appreciated that other embodiments may iteratively execute starting at any step. Moreover, when starting a successive iteration, the operations server may be configured to dynamically determine which particular step or process should be executed to start the next iteration.

Figure 4:
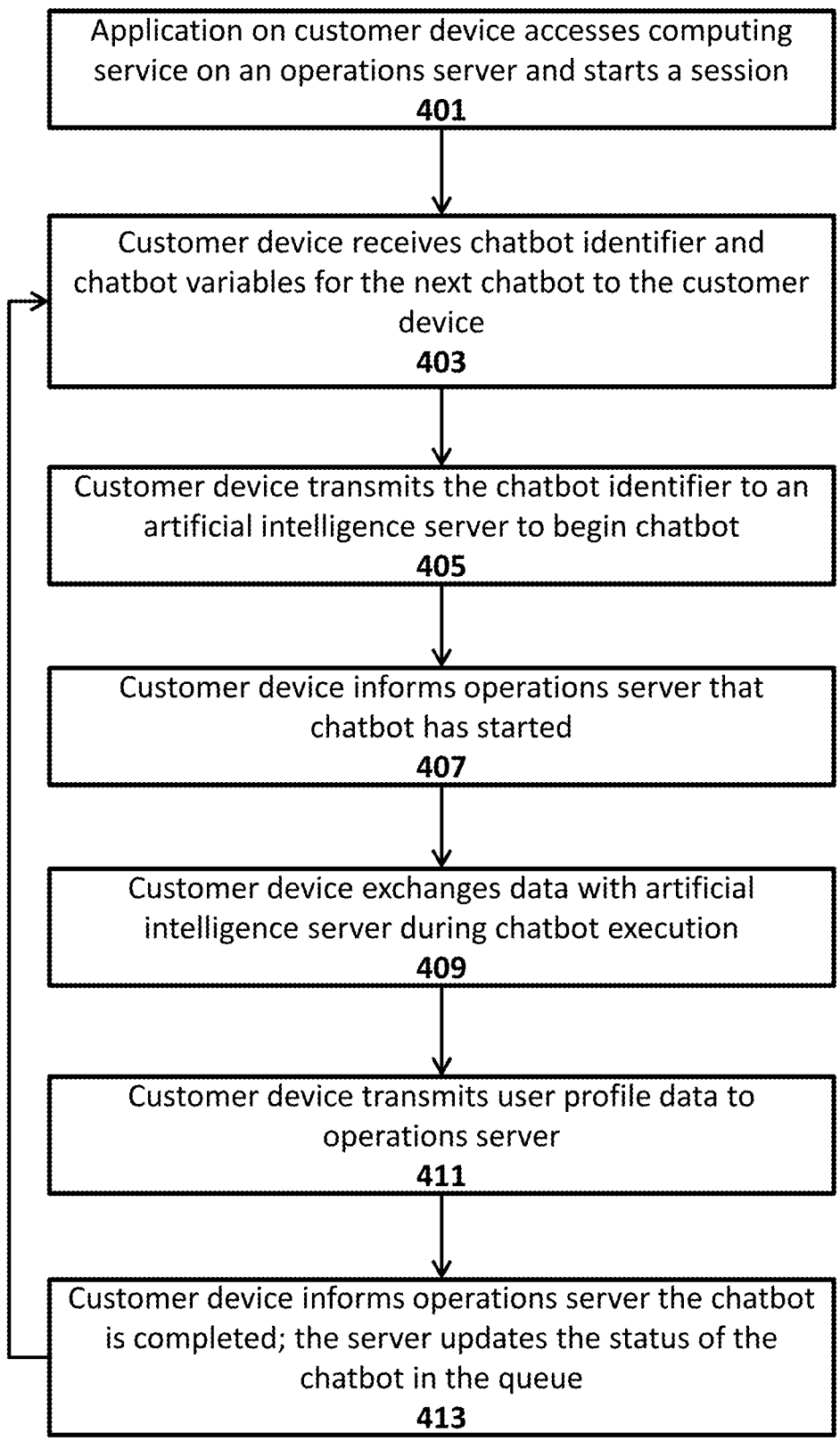
FIG. 4 shows execution of method for accessing a chatbot queue and executing chatbots by a customer device, according to an exemplary embodiment.

FIG. 4 shows execution of method 400 for accessing a chatbot queue and executing chatbots by a customer device, such as a mobile device. The exemplary method 400 comprises steps 401, 403, 405, 407, 409, 411, and 413. However, it should be appreciated that some embodiments may include additional or alternative steps, or may omit one or more steps, without departing from the scope of this disclosure. Execution steps may be divided according to design decisions that determine an amount of processing is required by a client device (e.g., customer device, coach computer) as compared to other devices of the digital therapy service (e.g., operations server). As such, in some embodiments, certain steps described herein as being executed by a customer device, may be executed by, for example, an operations server or other device. It can further be appreciated that each of the steps described herein could be logically broken into or viewed as sub-steps or sub-components of the steps mentioned.

In step 401, a therapeutic software application or sub-component of the therapeutic application on a customer device establishes a session when the customer device loads or accesses certain features of the digital therapy service, which may be executed or otherwise hosted on an operations server. In the exemplary method 400, after the customer has launched the software application on the customer device, and accesses a chatbot interface feature, the software application may establish a chatbot session with the operations server. In some instances, data related to the session may be captured and saved by an operations server in a customer data record of a customer database.

In step 403, the customer device receives, from an operations server, a chatbot identifier for a next chatbot to be implemented and related chatbot variable data.

In step 405, the customer device transmits the chatbot identifier or a chatbot to an artificial intelligence server with a request for the artificial intelligence server to begin executing the chatbot or the chatbot identified by the chatbot identifier in the request, where the request may include the chatbot identifier and any variable data. In some cases, before executing the chatbot, the artificial intelligence server may query an artificial intelligence database to retrieve the chatbot code identified by the chatbot identifier.

In step 407, the customer device transmits a status update to the operations server that the chatbot has started. The status update may contain status indicator data that corresponds to a data field in the chatbot queue. The operations server may update the status indicator data field to indicate the chatbot as having started.

In step 409, the customer device exchanges data with the artificial intelligence server during chatbot execution. The data received from the artificial intelligence server is based upon the code of the chatbot, as executed by the artificial intelligence server. The data may have any number of formats (e.g., text, video, audio, hyperlink, audiovisual) and may contain various types of content. This data may be outputted to a chatbot interface at a GUI of the customer device. Likewise, the customer may input various types of data into the chatbot interface at the GUI of the customer device. These inputs may be forwarded to the artificial intelligence server to continue processing through the chatbot code.

In step 411, the customer device may transmit data inputs to the operations server. The customer device may transmit various types of data inputs (e.g., journal entries, body metric measurements, indicator of interactions) to the operations server during or after chatbot execution. For example, the artificial intelligence server and customer device may execute a Logging Bot that accepts inputted data regarding certain tasks or behaviors performed by the customer (e.g., meal logs, exercise log). When this data is inputted into the chat interface GUI of the customer device, the customer device may transmit the data to the artificial intelligence server to continue execution of the chatbot, and also to the operations server. The operations server may then save this data into appropriate data fields of the customer data record.

In step 413, the customer device informs the operations server that the chatbot is completed; and the operations server updates the status of the chatbot in the queue to indicate the chatbot is completed. In particular the customer device may transmit a status update with an indicator that the chatbot is completed when the artificial intelligence server has completed executing the chatbot. The operations server may update the chatbot's data record in the customer's chatbot queue.

The exemplary method 400 may execute in iterations, starting each successive iteration at step 403, until, for example, the customer ends a chat session, the customer closes the software application, or the operations server determines there are no further chatbots to be implemented in the customer's chatbot queue. It should be appreciated that other embodiments may iteratively execute starting at any step.

Examples of chatbots may include:

Logging Bot—A chatbot that prompts a customer to input data related to tasks the customer was instructed to perform (e.g., dietary intake, exercise completed). An operations server or other computing device may add a Logging Chatbot to a customer's chatbot queue at predetermined times of the day. The operations server may then transmit the Logging Chatbot to the customer device at the time it is added to the queue or at a different predetermined time, such that the Logging Chatbot is automatically transmitted to the customer device at certain times of the day with respect to certain tasks the customer is assigned to perform, such as eating, exercising, collecting body metric measurement data, or other activities or tasks. The Logging Chatbot is thus received by the customer, for example, shortly after breakfast or lunchtime, and may prompt the customer to input, for example, data inputs related to the customer's meal or other assigned tasks.

For example, at or before a predetermined time in the morning, a chatbot generates an interface at the customer device. The outputs presented via a GUI interface (e.g., text, audio, video) may ask the customer whether their breakfast included food that is on the customer's meal plan. At a predetermined time in the afternoon, the same or different chatbot generates an interface with outputted data (e.g., text, audio, visual) asking about breakfast and/or lunch. And, at a predetermined time in the evening, typically after dinner time (e.g., 8:00 or 9:00), the same or different chatbot will generate an interface with data asking about breakfast, lunch, and/or dinner. Reponses may be logged into a corresponding data field of the customer database. If the data for a particular meal is available because the customer has already logged the information through a different interface, then the artificial intelligence server may determine that requesting information about the particular meal is unnecessary. In addition, if data is available for a particular meal because the customer has already logged the information through a different interface, then the operations server may determine that the chatbot is completed or invalid based on a query of the customer database. The operations server may be triggered to add the logging chatbot to the queue several times a day, if the customer has not already logged the information requested by the chatbot (e.g., meal data, exercise data).

Summary Bot—A chatbot that provides a customer with a summary of an interaction with personnel of the digital therapy provider (e.g., coach, health specialist, help desk or system administrator). For example, after a telephone call with a coach, the coach may use an interface of the coach computer to input data (e.g., text, audio, visual) containing a summary for the telephone call, which may be logged into the customer database. A summary chatbot may provide the data containing the summary to the customer through a chatbot interface.

Call Schedule Bot—A chatbot that prompts a customer to schedule a telephone call with a coach or other personnel of the digital therapy provider. For example, a call schedule chatbot may generate an interface prompting the customer to schedule a meeting with their coach, and may contain an input field that accepts input data indicating a date/time to for the call or other information. The operations server may be triggered to add the call schedule chatbot to the chatbot queue at a predetermined interval or after a predetermined event (e.g., after determining that a Summary Bot has been completed). The call schedule chatbot may instruct a device of the system (e.g., customer device, operations server, artificial intelligence server) to query an application server hosting a calendar program for the coach, and may provide suggested times to the customer via the interface.

Reflection Bot—after a call with a coach or other event (e.g., exercise, meal), and/or at a predetermined interval, a reflection chatbot may be sent to the customer prompting the customer to input data via an interface (e.g., text, audio, visual) reflecting on the call or other event. The inputted data containing the customer's response may be added the customer database.

It should be understood that, throughout this disclosure, stream-oriented connections and/or protocols, including, but not limited to, Quick UDP Internet Connection, UDP Torrent tracker and Stream Control Transmission Protocol may be used in a similar manner as a TCP connection and/or protocol. Additionally, all the protocols running on top of the aforementioned stream-oriented connections and/or protocols, including, but not limited to, HTTP, HTTPS and SPDY, may use features described within the context of the present disclosure by being implemented on top of the applicable stream-oriented connections and/or protocol.

The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

The disclosure is also directed to computer program products comprising software stored on any computer useable medium. Such software, when executed in one or more data processing device, causes a data processing device(s) to operate as described herein. Embodiments of the disclosure employ any computer useable or readable medium, known now or in the future. Examples of computer useable mediums include, but are not limited to, primary storage devices (e.g., any type of random access memory), secondary storage devices (e.g., hard drives, SSDs, floppy disks, tapes, magnetic storage devices, optical storage devices, MEMS, nano-technological storage device, Flash, etc.), and communication mediums (e.g., wired and wireless communications networks, local area networks, wide area networks, intranets, etc.).

It is to be understood that the various embodiments disclosed herein are not mutually exclusive and that a particular implementation may include features or capabilities of multiple embodiments discussed herein.

While the present disclosure refers to packets and/or fields within packets by certain specific names, it is to be understood that these names are not intended to limit the scope of the invention in any way and that any name or designator may be given to packets and/or fields described herein as long as it performs the function and/or serves the purpose described herein. It is also to be understood that the invention is not limited to any particular structure and/or organization of packets and/or fields therein.

While specific embodiments and applications of the present invention have been illustrated and described, it is to be understood that the invention is not limited to the precise configuration and components disclosed herein. The terms, descriptions and figures used herein are set forth by way of illustration only and are not meant as limitations. Various modifications, changes, and variations which will be apparent to those skilled in the art may be made in the arrangement, operation, and details of the apparatuses, methods and systems of the present invention disclosed herein without departing from the spirit and scope of the invention. By way of non-limiting example, it will be understood that the block diagrams included herein are intended to show a selected subset of the components of each apparatus and system, and each pictured apparatus and system may include other components which are not shown on the drawings. Additionally, those with ordinary skill in the art will recognize that certain steps and functionalities described herein may be omitted or re-ordered without detracting from the scope or performance of the embodiments described herein.

The various illustrative logical blocks, modules, circuits, and algorithm steps described in connection with the embodiments disclosed herein may be implemented as electronic hardware, computer software, or combinations of both. To illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application—such as by using any combination of microprocessors, microcontrollers, field programmable gate arrays (FPGAs), application specific integrated circuits (ASICs), and/or System on a Chip (SoC)—but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

What is claimed is:

1. A computer-implemented method for generating and monitoring a therapy regimen, the method comprising:
   receiving, by a computer, from one or more devices associated with a user a plurality of initial inputs and an indicator of a condition of the user, wherein at least one of the devices is a mobile device, and wherein each respective initial input contains a value;
   storing, by the computer, each value of the plurality of initial inputs into a database that is configured to store one or more database records of the user;
   providing the therapy regimen to a software application loaded on the one or more devices associated with a user, based upon the condition of the user; and
   generating, by machine learning software within the computer, a health score of the user based at least in part on interactions between the user and aspects of the software application, one or more values stored in a database record of the user, and the condition associated with the user, wherein the computer receives indicators of the interactions and tracks the amount of interactions between the user and the software application, the health score of the user being generated by applying a health score model associated with the condition and indicating one or more of parameters and relative weights for the parameters, the health score model trained by the machine learning software using historical data for individuals having the condition associated with the user.

2. The method of claim 1, wherein generating the health score of the user further comprises generating, by the machine learning software within the computer, the health score model associated with the condition according to a statistical analysis of one or more types of data stored in a plurality of database records of the database, and
wherein the health score model is configured to determine the health score associated with the condition of the user using: the amount of interactions between the user and the software application and one or more types of data corresponding respectively to a set of the one or more values for the one or more data inputs stored in the database record of the user.

3. The method of claim 2, further comprising retraining, by the machine learning software within the computer, the health score model associated with the condition in response to the database storing a predetermined number of additional database records.

4. The method of claim 3, wherein the predetermined number of additional database records comprises records of a predetermined number of customers having completed or participated for a predetermined time in the therapy regimens for the condition associated with the user.

5. The method of claim 4, wherein the condition of the user is type II diabetes.

6. The method of claim 2, further comprising updating, by the computer, the health score model associated with the condition at predetermined time intervals.

7. The method of claim 1, further comprising:
selecting, by the computer, a chatbot identifier for a corresponding chatbot for the software application to implement according to the therapy regimen; and
updating, by the computer, a chatbot queue of the user to include the chatbot identifier.

8. The method of claim 7, further comprising transmitting, by the computer, to the software application of the user a next chatbot identifier in the chatbot queue, wherein the chatbot queue of the user contains one or more chatbot identifiers corresponding respectively to one or more chatbots for the software application to implement.

9. The method of claim 1, wherein the health score is further based upon a frequency of receiving each of the data inputs indicating interactions between the user and the software application.

10. The method of claim 1, wherein receiving the plurality of data inputs further comprises storing, by the computer, each value of the plurality of data inputs into the one or more database records of the user.

11. The method of claim 1, wherein a device of the one or more devices is selected from the group comprising: a smart home device, a wearable device, and a fitness tracker.

12. The method of claim 1, wherein the condition of the user is a diabetes health condition.

13. The method of claim 1, wherein the health score model is trained with and uses data fields relevant to monitoring diabetes.

14. The method of claim 13, wherein the data fields are selected from the group consisting of blood glucose, cholesterol, blood pressure, weight, and number of interactions with one or more of the one or more devices and a coach.

15. The method of claim 1, wherein the machine learning software executes machine learning algorithms and processes selected from the group consisting of generalized linear models, random forests, support vector machines, unsupervised and/or supervised clustering, and deep learning, wherein deep learning includes neural networks.

16. The method of claim 1, further comprising comparing, by the computer, one or more data fields relevant to the user's condition against pre-stored milestone parameters or data values at predetermined milestone intervals, wherein the prestored milestone values may operate as threshold values.

17. The method of claim 16, wherein there are multiple pre-stored milestone values for multiple data fields, to compare multiple different customer values of different fields against multiple different pre-stored values.

18. The method of claim 16, further comprising automatically adjusting, by the computer, features and/or resources provided to the user based upon one or more of the updated health score and the achievement milestone comparisons.

19. The method of claim 18, wherein said resources comprise meeting time with one or more coaches and/or specialist personnel.

20. The method of claim 1, further comprising:
receiving, by the computer, a plurality of data inputs from the one or more devices, wherein at least one data input indicates an interaction between the user and the software application, and wherein each respective data input contains a value; and
updating, by the computer, the health score of the user using the one or more data inputs and an amount of interactions between the user and the software application to provide an updated health score.

21. The method of claim 20, further comprising updating, by the computer, the therapy regimen of the user based upon the updated health score that is updated using the one or more data inputs and the amount of interactions.

22. The method of claim 21, wherein updating the therapy regimen of the user further comprises transmitting, by the computer, the updated therapy regimen to the software application of the user.

23. The method of claim 1, wherein the software application is on the mobile device.

24. An apparatus for generating and monitoring a therapy regimen, the apparatus comprising:
a processor configured to:
receive, from one or more devices associated with a user, a plurality of initial inputs and an indicator of a condition of the user, wherein at least one of the devices is a mobile device, and wherein each respective initial input contains a value;
store each value of the plurality of initial inputs into a database that is configured to store one or more database records of the user;
provide the therapy regimen to a software application on the one or more devices associated with a user, based upon the condition associated with the user;
generate, by machine learning software within the processor, a health score of the user based at least in part on interactions between the user and aspects of the software application, one or more values stored in a database record of the user, and the condition associated with the user, wherein the processor receives indicators of the interactions and tracks the amount of interactions between the user and the software application, the health score being generated by applying a health score model associated with the condition and indicating one or more of parameters and relative weights for the parameters, the health score model trained by the machine learning software using historical data for individuals having the condition associated with the user.

25. The apparatus of claim 24, wherein the processor is further configured to generate, by the machine learning software within the processor, the health score model associated with the condition according to a statistical analysis of one or more types of data stored in a plurality of database records of the database, and wherein the health score model is configured to determine the health score associated with the condition of the user using: the amount of interactions between the user and the software application and one or more types of data corresponding respectively to a set of the one or more values for the one or more data inputs stored in the database record of the user.

26. The apparatus of claim 25, wherein the processor is further configured to retrain, by the machine learning software within the processor, the health score model associated with the condition in response to the database storing a predetermined number of additional database records.

27. The apparatus of claim 26, wherein the predetermined number of additional database records comprises records of a predetermined number of customers having completed or participated for a predetermined time in the therapy regimens for the condition associated with the user.

28. The apparatus of claim 27, wherein the condition of the user is type II diabetes.

29. The apparatus of claim 25, wherein the processor is further configured to update the health score model associated with the condition at predetermined time intervals.

30. The apparatus of claim 24, wherein the processor is further configured to:

select a chatbot identifier for a corresponding chatbot for the software application to implement according to the therapy regimen; and update a chatbot queue of the user to include the chatbot identifier.

31. The apparatus of claim 30, wherein the processor is further configured to transmit to the software application of the user a next chatbot identifier in the chatbot queue, wherein the chatbot queue of the user contains one or more chatbot identifiers corresponding respectively to one or more chatbots for the software application to implement.

32. The apparatus of claim 24, wherein the health score is further based upon a frequency of receiving each of the data inputs indicating interactions between the user and the software application.

33. The apparatus of claim 24, wherein the processor is further configured to store each value of the plurality of data inputs into the one or more database records of the user.

34. The apparatus of claim 24, wherein a device of the one or more devices is selected from the group comprising: a smart home device, a wearable device, and a fitness tracker.

35. The apparatus of claim 24, wherein the condition of the user is a diabetes health condition.

36. The apparatus of claim 24, wherein the health score model is trained with and uses data fields relevant to monitoring diabetes.

37. The apparatus of claim 36, wherein the data fields are selected from the group consisting of blood glucose level, cholesterol, blood pressure, weight, and number of interactions with one or more of the one or more devices and a coach.

38. The apparatus of claim 24, wherein the machine learning software executes machine learning algorithms and processes selected from the group consisting of generalized linear models, random forests, support vector machines, unsupervised and/or supervised clustering, and deep learning, wherein deep learning includes neural networks.

39. The apparatus of claim 24, wherein the processor is further configured to compare one or more data fields relevant to the user's condition against pre-stored milestone parameters or data values at predetermined milestone intervals, wherein the prestored milestone values may operate as threshold values.

40. The apparatus of claim 39, wherein there are multiple pre-stored milestone values for multiple data fields, to compare multiple different customer values of different fields against multiple different pre-stored values.

41. The apparatus of claim 39, wherein the processor is further configured to automatically adjust features and/or resources provided to the user based upon one or more of the updated health score, and the achievement milestone comparisons.

42. The apparatus of claim 41, wherein said resources comprise meeting time with one or more coaches and/or specialist personnel.

43. The apparatus of claim 24, wherein the processor is further configured to:

receive a plurality of data inputs from the one or more devices, wherein at least one data input indicates an interaction between the user and the software application, and wherein each respective data input contains a value; and update the health score of the user using the one or more data inputs and an amount of interactions between the user and the software application to provide an updated health score.

44. The apparatus of claim 43, wherein the processor is further configured to update the therapy regimen of the user based upon the updated health score that is updated using the one or more data inputs and the amount of interactions.

45. The apparatus of claim 44, wherein the processor is further configured to transmit the updated therapy regimen to the software application of the user.

46. The apparatus of claim 24, wherein the software application is on the mobile device.

47. A computer-implemented method for generating and monitoring a therapy regimen, comprising:

receiving, by a computer, from one or more devices associated with a user a request to generate a therapy regimen for a customer, said request comprising a plurality of initial inputs and an indicator of a condition of the customer, wherein at least one of the devices is a customer mobile device, and wherein each respective initial input contains a value;

storing, by the computer, each value of the plurality of initial inputs into a database that is configured to store one or more database records of the customer;

generating a therapy regimen based upon the data of the request, wherein the therapy regimen comprises one or more machine executable instructions;

transmitting the therapy regimen to a software application on one or more customer devices, based on the condition associated with the customer;

generating, by machine learning software within the computer, a health score of the customer based at least in part on interactions between the customer and aspects of the software application, one or more values stored in a database record of the customer, and the condition associated with the customer, wherein the computer receives indicators of the interactions as part of the data and tracks the amount of interactions between the customer and the software application, the health score of the customer being generated by applying a health score model associated with the condition and indicating one or more of parameters and relative weights for the parameters, the health score model trained by the machine learning software using historical data for individuals having the condition associated with the customer.

48. The method according to claim 47, further comprising:
receiving, by the computer, a plurality of data inputs from the one or more devices, wherein at least one data input indicates an interaction between the customer and the software application, and wherein each respective data input contains a value; and
updating the health score of the customer using the one or more data inputs and an amount of interactions between the customer and the software application to provide an updated health score.

49. The method of claim 48, further comprising updating, by the computer, the therapy regimen of the customer based upon the updated health score that is updated using the one or more data inputs and the amount of interactions.

50. The method of claim 49, wherein updating the therapy regimen of the customer further comprises transmitting, by the computer, the updated therapy regimen to the software application.

51. The method of claim 47, wherein the software application is on the mobile device.

52. The method of claim 47, wherein generating the health score of the customer further comprises generating, by the machine learning software within the computer, the health score model associated with the condition according to a statistical analysis of one or more types of data stored in a plurality of database records of the database, and
wherein the health score model is configured to determine the health score associated with the condition of the customer using: the amount of interactions between the customer and the software application and one or more types of data corresponding respectively to a set of the one or more values for the one or more data inputs stored in the database record of the customer.

53. The method of claim 47, further comprising retraining, by the machine learning software within the computer, the health score model associated with the condition in response to the database storing a predetermined number of additional database records.

54. The method of claim 53, wherein the predetermined number of additional database records comprises records of a predetermined number of customers having completed or participated for a predetermined time in the therapy regimens for the condition associated with the customer.

55. The method of claim 54, wherein the condition of the customer is type II diabetes.

56. The method of claim 47, further comprising updating, by the computer, the health score model associated with the condition at predetermined time intervals.

57. The method of claim 47, further comprising:
selecting, by the computer, a chatbot identifier for a corresponding chatbot for the software application to implement according to the therapy regimen; and
updating, by the computer, a chatbot queue of the customer to include the chatbot identifier.

58. The method of claim 57, further comprising transmitting, by the computer, to the software application of the customer a next chatbot identifier in the chatbot queue, wherein the chatbot queue of the customer contains one or more chatbot identifiers corresponding respectively to one or more chatbots for the software application to implement.

59. The method of claim 47, wherein the health score is further based upon a frequency of receiving each of the data inputs indicating interactions between the customer and the software application.

60. The method of claim 47, wherein receiving the plurality of data inputs further comprises storing, by the computer, each value of the plurality of data inputs into the one or more database records of the customer.

61. The method of claim 47, wherein the condition of the customer is a diabetes health condition.

62. The method of claim 47, wherein the health score model is trained with and uses data fields relevant to monitoring diabetes.

63. The method of claim 62, wherein the data fields are selected from the group consisting of blood glucose, cholesterol, blood pressure, weight, and number of interactions with one or more of the one or more devices and a coach.

64. The method of claim 47, wherein the machine learning software executes machine learning algorithms and processes selected from the group consisting of generalized linear models, random forests, support vector machines, unsupervised and/or supervised clustering, and deep learning, wherein deep learning includes neural networks.

65. The method of claim 47, further comprising comparing, by the computer, one or more data fields relevant to the customer's condition against pre-stored milestone parameters or data values at predetermined milestone intervals, wherein the prestored milestone values may operate as threshold values.

66. The method of claim 65, wherein there are multiple pre-stored milestone values for multiple data fields, to compare multiple different customer values of different fields against multiple different pre-stored values.

67. The method of claim 65, further comprising automatically adjusting, by the computer, features and/or resources provided to the customer based upon one or more of the updated health score and the achievement milestone comparisons.

68. The method of claim 47, wherein the data for the request is manually input by the customer and/or a coach.

69. An apparatus for generating and monitoring a therapy regimen, the apparatus comprising:
a processor configured to:
receive, from one or more devices associated with a user a request to generate a therapy regimen for a customer, said request comprising a plurality of initial inputs and an indicator of a condition of the customer, wherein at least one of the devices is a mobile device, and wherein each respective initial input contains a value;
store each value of the plurality of initial inputs into a database that is configured to store one or more database records of the customer;
generate a therapy regimen based upon the data of the request, wherein the therapy regimen comprises one or more machine executable instructions;
transmit the therapy regimen to a software application on one or more customer devices, based upon the condition associated with the customer;
generate, by machine learning software within the processor, a health score of the customer based at least in part on interactions between the customer and aspects of the software application, one or more values stored in a database record of the customer, and the condition associated with the customer, wherein the processor receives indicators of the interactions and tracks the amount of interactions between the customer and the software application, the health score being generated by applying a health score model associated with the condition and indicating one or more of parameters and relative weights for the parameters, the health score model trained by the machine learning software using historical data for individuals having the condition associated with the customer.

70. The apparatus of claim 69, wherein the processor is further configured to:
receive a plurality of data inputs from the one or more devices, wherein at least one data input indicates an interaction between the customer and the software application, and wherein each respective data input contains a value; and
update the health score of the customer using the one or more data inputs and an amount of interactions between the customer and the software application to provide an updated health score.

71. The apparatus of claim 70, wherein the processor is further configured to update the therapy regimen of the customer based upon the updated health score that is updated using the one or more data inputs and the amount of interactions.

72. The apparatus of claim 71, wherein the processor is further configured to transmit the therapy regimen to the software application.

73. The apparatus of claim 69, wherein the software application is on the mobile device.

74. The apparatus of claim 69, wherein the processor is further configured to generate, by the machine learning software within the processor, the health score model associated with the condition according to a statistical analysis of one or more types of data stored in a plurality of database records of the database, and
wherein the health score model is configured to determine the health score associated with the condition of the customer using: the amount of interactions between the customer and the software application and one or more types of data corresponding respectively to a set of the one or more values for the one or more data inputs stored in the database record of the customer.

75. The apparatus of claim 74, wherein the processor is further configured to retrain, by the machine learning software within the processor, the health score model associated with the condition in response to the database storing a predetermined number of additional database records.

76. The apparatus of claim 75, wherein the predetermined number of additional database records comprises records of a predetermined number of customers having completed or participated for a predetermined time in the therapy regimens for the condition associated with the customer.

77. The apparatus of claim 76, wherein the condition of the customer is type II diabetes.

78. The apparatus of claim 74, wherein the processor is further configured to update the health score model associated with the condition at predetermined time intervals.

79. The apparatus of claim 69, wherein the processor is further configured to:
select a chatbot identifier for a corresponding chatbot for the software application to implement according to the therapy regimen; and
update a chatbot queue of the customer to include the chatbot identifier.

80. The apparatus of claim 79, wherein the processor is further configured to transmit to the software application of the customer a next chatbot identifier in the chatbot queue, wherein the chatbot queue of the customer contains one or more chatbot identifiers corresponding respectively to one or more chatbots for the software application to implement.

81. The apparatus of claim 69, wherein the health score is further based upon a frequency of receiving each of the data inputs indicating interactions between the customer and the software application.

82. The apparatus of claim 69, wherein the processor is further configured to store each value of the plurality of data inputs into the one or more database records of the customer.

83. The apparatus of claim 69, wherein the condition of the customer is a diabetes health condition.

84. The apparatus of claim 69, wherein the health score model is trained with and uses data fields relevant to monitoring diabetes.

85. The apparatus of claim 84, wherein the data fields are selected from the group consisting of blood glucose level, cholesterol, blood pressure, weight, and number of interactions with one or more of the one or more devices and a coach.

86. The apparatus of claim 69, wherein the machine learning software executes machine learning algorithms and processes selected from the group consisting of generalized linear models, random forests, support vector machines, unsupervised and/or supervised clustering, and deep learning, wherein deep learning includes neural networks.

87. The apparatus of claim 69, wherein the processor is further configured to compare one or more data fields relevant to the customer's condition against pre-stored milestone parameters or data values at predetermined milestone intervals, wherein the prestored milestone values may operate as threshold values.

88. The apparatus of claim 87, wherein there are multiple pre-stored milestone values for multiple data fields, to compare multiple different customer values of different fields against multiple different pre-stored values.

89. The apparatus of claim 87, wherein the processor is further configured to automatically adjust features and/or resources provided to the customer based upon one or more of the updated health score, and the achievement milestone comparisons.

90. The apparatus of claim 69, wherein the data for the request is manually input by the customer and/or a coach.

* * * * *